United States Patent
Dunkley et al.

(10) Patent No.: US 9,943,584 B2
(45) Date of Patent: Apr. 17, 2018

(54) **NON-TYPEABLE *HAEMOPHILUS INFLUENZAE* VACCINES AND THEIR USES**

(75) Inventors: Margaret Lorraine Dunkley, New South Wales (AU); Robert Llewellyn Clancy, Newcastle (AU)

(73) Assignee: HUNTER IMMUNOLOGY LIMITED, Brighton Vic (AU)

(*) Notice: Subject to any disclaimer, the term of this patent is extended or adjusted under 35 U.S.C. 154(b) by 643 days.

(21) Appl. No.: 13/059,185

(22) PCT Filed: Sep. 17, 2009

(86) PCT No.: PCT/IB2009/007303
§ 371 (c)(1),
(2), (4) Date: May 4, 2011

(87) PCT Pub. No.: WO2010/032141
PCT Pub. Date: Mar. 25, 2010

(65) Prior Publication Data
US 2011/0206765 A1    Aug. 25, 2011

Related U.S. Application Data

(60) Provisional application No. 61/097,729, filed on Sep. 17, 2008.

(51) Int. Cl.

| | |
|---|---|
| *A61K 39/02* | (2006.01) |
| *A61K 39/102* | (2006.01) |
| *A61F 13/00* | (2006.01) |
| *A61K 45/00* | (2006.01) |
| *A61K 9/48* | (2006.01) |
| *A61K 39/00* | (2006.01) |
| *A61K 39/38* | (2006.01) |
| *A61K 9/20* | (2006.01) |
| *A61K 9/28* | (2006.01) |
| A61K 35/74 | (2015.01) |
| A61K 9/00 | (2006.01) |
| C07K 14/285 | (2006.01) |
| A61K 38/00 | (2006.01) |
| A61K 39/39 | (2006.01) |

(52) U.S. Cl.
CPC ............ *A61K 39/102* (2013.01); *A61K 9/20* (2013.01); *A61K 9/28* (2013.01); *A61K 9/0043* (2013.01); *A61K 9/4891* (2013.01); *A61K 35/74* (2013.01); *A61K 38/00* (2013.01); *A61K 39/00* (2013.01); *A61K 39/39* (2013.01); *A61K 2039/521* (2013.01); *C07K 14/285* (2013.01)

(58) Field of Classification Search
None
See application file for complete search history.

(56) References Cited

U.S. PATENT DOCUMENTS

| | | | |
|---|---|---|---|
| 4,873,090 A | 10/1989 | Clancy | |
| 6,455,052 B1 | 9/2002 | Marcussen et al. | |
| 7,115,271 B1* | 10/2006 | Forsgren | 424/256.1 |
| 7,858,073 B2 | 12/2010 | Clancy et al. | |
| 2008/0044843 A1 | 2/2008 | Perlee et al. | |
| 2008/0108079 A1 | 5/2008 | Chissoe | |
| 2008/0181932 A1* | 7/2008 | Bortz et al. | 424/439 |

FOREIGN PATENT DOCUMENTS

| | | |
|---|---|---|
| EP | 0680765 B1 | 3/2007 |
| WO | 94/20070 A1 | 9/1994 |
| WO | 96/05858 A1 | 2/1996 |
| WO | 2005077409 A1 | 8/2005 |
| WO | 2005096823 A1 | 10/2005 |
| WO | WO 2006/017895 A1 * | 2/2006 |
| WO | 2008/109956 A1 | 9/2008 |
| WO | 2008/109957 A1 | 9/2008 |

OTHER PUBLICATIONS

Hashmat et al., AAPS Pharm SciTech, Mar. 2008; 9(1): 116-121.*
Mayo clinic; http://www.mayoclinic.com/health/cystic-fibrosis/DS00287/DSECTION=treatments-and-drugs; accessed Oct. 25, 2013.*
Mackay et al., Immunol Allergy Clin N Am, 2013; 33: 95-115.*
Cripps et al., Immunology and Cell Biology, Aug. 2008; 86: 557-561.*
Yusuke Abe et al., "Lymphocyte Proliferative Response to P6 of Haemophilus influenzae Is Associated with Relative Protection from Exacerbations of Chronic Obstructive Pulmonary Disease", American Journal of Respiratory and Critical Care Medicine, 2002, pp. 967-971, vol. 165, Duplicate from IDS filed Jun. 21, 2011.
Hans Bisgaard et al., "Childhood Asthma after Bacterial Colonization of the Airway in Neonates", The New England Journal of Medicine, Oct. 11, 2007, pp. 1487-1495, vol. 357—issue No. 15, Massachusetts Medical Society.
P. Clementsen et al., "Endotoxin from Haemophilus influenzae enhances IgE-mediated and non-immunological histamine release", Allergy, 1990, pp. 10-17, vol. 45, Duplicate from IDS filed Jun. 21, 2011.
Deirdre Donnelly et al., "Outcomes in children treated for persistent bacterial bronchitis", Thorax, 2007, pp. 80-84, vol. 62.
Foxwell AR et al., "Haemophilus influenzae oral whole cell vaccination for preventing acute exacerbations of chronic bronchitis (Review)", The Cochrane Collaboration, 2007, pp. 1-15, Issue 4, John Wiley & Sons, Ltd.
T H Harju et al., "Pathogenic bacteria and viruses in induced sputum or pharyngeal secretions of adults with stable asthma", Thorax, 2006, pp. 579-584, vol. 61.

(Continued)

*Primary Examiner* — Gary Nickol
*Assistant Examiner* — Lakia Jackson-Tongue
(74) *Attorney, Agent, or Firm* — Pergament & Cepeda LLP; Milagros A. Cepeda; Edward D. Pergament

(57) ABSTRACT

Provided are non-typeable *Haemophilus influenzae* vaccines useful for the treatment of chronic obstructive pulmonary disease and asthma in a patient. In certain aspects, the vaccine is a monobacterial vaccine. Bacterial strains for use in the vaccines of the present application are also provided.

35 Claims, 20 Drawing Sheets

(56) References Cited

OTHER PUBLICATIONS

KJ Aergard et al., "Basophil-bound IgE and serum IgE directed against Haemophilus influenzae and *Streptococcus pneumoniae* in patients with chronic bronchitis during acute exacerbations", APMIS, 1996, pp. 61-67, vol. 104.

Jun Koyoma et al., "Strain-Specific Pulmonary Defense Achieved after Repeated Airway Immunizations with Non-Typeable Haemophilus Influenzae in a Mouse Model", Tohoku J. Exp. Med., 2007, pp. 63-74, vol. 211.

Lambert and Stern, "Infective Factors in Exacerbations of Bronchitis and Asthma", British Medical Journal, Aug. 5, 1972, pp. 323-327, vol. 3.

Irini Lazou Ahren et al., "Nontypeable Haemophilus influenzae Activates Human Eosinophils through β-Glucan Receptors", American Journal of Respiratory Cell and Molecular Biology, 2003, pp. 598-605, vol. 29.

Karen McCoy et al., "Predicting episodes of poor asthma control in treated patients with asthma", J Allergy Clin. Immunol., 2006, pp. 1226-1233, vol. 118—issue No. 6, Duplicate from IDS filed Jun. 21, 2011.

Lieke V. M. Moller et al., "Haemophilus Influenzae in Lung Explants of Patients with End-stage Pulmonary Disease", American Journal of Respiratory and Critical Care Medicine, 1998, pp. 950-956, vol. 157.

Venkata Bandi et al., "Nontypeable Haemophilus influenzae in the Lower Respiratory Tract of Patients with Chronic Bronchitis", American Journal of Respiratory and Critical Care Medicine, 2001, pp. 2114-2119, vol. 164.

Timothy F. Murphy et al., "Persistent Colonization by Haemophilus influenzae in Chronic Obstructive Pulmonary Disease", American Journal of Respiratory and Critical Care Medicine, 2004, pp. 266-272, vol. 170.

Nagayama Y et al., "Bacterial colonization in respiratory secretions from acute and recurrent wheezing infants and children", Pediatric Allergy and Immunology, 2007, pp. 110-117, vol. 18, Journal Compilation, Blackwell Munksgaard.

D-H. Nahm et al., "Elevation of specific immunoglobulin A antibodies to both allergen and bacterial antigen in induced sputum from asthmatics", European Respiratory Journal, 1998, pp. 540-545, vol. 12, ERS Journals Ltd.

M. Bud Nelson et al., "Cloning and Sequencing of Haemophilus influenzae Outer membrane Protein P6", Infection and Immunity, Jan. 1988, pp. 128-134, vol. 56—issue No. 1, American Society for Microbiology.

DM Patrick et al., "Severe exacerbations of COPD and asthma. Incremental benefit of adding ipratropium to usual theraphy", Chest, Aug. 1990, pp. 295-297, vol. 98—issue No. 2, American College of Chest Physicians.

Wytske Fokkens et al., "European Position Paper on Rhinosinusitis and Nasal Polyps 2007", Rhinology, 2007, pp. 1-136, vol. 45, suppl. 20, European Position Paper on Rhinosinusitis and Nasal Polyps group.

Sethi and Murphy, "Bacterial Infection in Chronic Obstructive Pulmonary Disease in 2000: a State-of-the-Art Review", Clinical Microbiology Reviews, Apr. 2001, pp. 336-363, vol. 14—issue No. 2, American Society for Microbiology.

Jodie L. Simpson et al., "Inflammatory subtypes in asthma: assessment and identification using induced sputum", Respirology, 2006, pp. 54-61, vol. 11.

Stallworth et al., "Antibiotic use in children who have asthma: results of retrospective database analysis", Journal of Managed Care Pharmacy, Oct. 2005, pp. 657-662, vol.11—issue No. 8. (Abstract), Duplicate from IDS filed Jun. 21, 2011.

B Stenius-Aarniala et al., "Lack of clinical exacerbations in adults with chronic asthma after immunization with killed influenza virus", Chest, Jun. 1986, pp. 786-789, vol. 89—issue No. 6, American College of Chest Physicians.

R. D. Tee and J. Pepys, "Specific serum IgE antibodies to bacterial antigens in allergic lung disease", Clinical Allergy, 1982, pp. 439-450, vol. 12, Blackwell Scientific Publications.

Sally E Wenzel, "Asthma: defining of the persistent adult phenotypes", Lancet, Aug. 26, 2006, pp. 804-813, vol. 368.

Yan-Ping Yang et al., "Nasopharyngeal Colonization with Nontypeable Haemophilus influenzae in Chinchillas", Infection and Immunity, May 1998, pp. 1973-1980, vol. 66—issue No. 5, American Society for Microbiology, Duplicate from IDS filed Jun. 21, 2011.

Sethi, et al.,"Bacterial Infection in Chronic Obstructive Pulmonary Disease in 2000: a State-Of-The Art Review", Clin. Microbiol. Rev., 2001,14:336-363.

Moller, et al.,"Haemophilus Influenzae in Lung Explants of Patients with End-Stage Pulmonary Disease", Am. J. Respir. Crit. Care med., 1998, 157:950-956.

Murphy, et al.,"Persistent Colonization by Haemophilus Influenzae in Chronic Obstructive Pulmonary Disease", Am. J. Respir. Crit. Care Med., 2004, 170: 266-272.

Clementsen, et al.,"Endotoxin from Haemophilus Influenzae Enhances IgE-mediated and Non-Immunological Histamine Release", Alergy 1990, 45: 10-17.

Kjaergard, et al.,"Basophil-Bound IgE and Serum IgE directed Against Haemophilus Influenzae and *Streptococcus pneumoniae* in Patients with Chronic Bronchitis During Acute Exacerbations", APMIS, 1996, 104; 61-67.

Tee, et al., "Specific Serum IgE Antibodies to Bacterial Antigens in Allergic Lung Disease", Clin. Allergy, 1982, 12: 439-450.

Nelson, et al., "Cloning and Sequencing of Haemophilus Influenzae Outer Membrane Protein P6", Infect. Immun., 1998, 56: 128-134.

Abe, et al., "Lymphocyte Profiferative Response to P6 of Haemophilus Influenzae is Associated with Relative Protection from Exacerbations of Chronic Obstructive Pulmonary Disease", Am. J. Respir. Crit. Care Med., 2002, 165: 967-971.

Foxwell A.R., et al. Haemophilus Influenza Oral Whole Cell Vaccination for Preventing Acute Exacerbation of Chronic Bronchitis (review), Cochrane Database of Systematic Reviews, (2006), Issue 4, pp. 1-18.

Moore, et al., "Viral Co-Infection Does Not Reduce the Efficacy of Vaccination Against Non-Typeable Haemophilus inflenzae Middle Ear Infection in a Rat Model", Journal of Otorhinolaryngol Relat Spec., (2001). vol. 63, No. 2, pp. 96-101.

Koyama J., et al., Strain-Specific Pulmonary Defense Achieved After Repeated Airway Immunizations with Non-Typeable Haemophilus Influenzae in a Mouse Model, The Tohoku Journal of Experimental Medicine (2007) vol. 211, pp. 63-74.

Yang Y., et al., "Nasopharyngeal Colonization with Nontypeable Haemophilus influenzae in Chinchillas". Infection and Immunity (1998) vol. 66, No. 5, pp. 1973-1980.

International Search Report dated Mar. 18, 2010 from corresponding International Application No. PCT/IB2009/007303.

International Preliminary Report on Patentability dated Mar. 22, 2011 from corresponding International Application No. PCT/IB2009/007303.

Donnelly D, et al., "Outcomes in Children Treated for Persistent Bacterial Bronchitis", Thorax, 2007, 62: 80-84.

Glauber J.H., et al., "Relationship Between Asthma Medication and Antibiotic Use", Chest, 2001, 120: 1485-1492.

Harju T.H., et al., "Pathogenic Bacteria and Viruses in Induced Sputum or Pharyngeal Secretions of Adults with Stable Asthma", Thorax, 2006, 61: 579-584.

Lambert H.P., et al., "Infective Factors in Exacerbations of Bronchitis and Asthma", British Medical Journal, 1972 3:323-327.

Lazou I., et al., "Nontypeable Haemophilus Influenzae Activates Human Eosinophils Through B-Glucan Receptors", Am. J. Respir. Cell Mol. Biol., 2003, 29: 598-605.

McCoy K., et al., "Predicting Episodes of Poor Asthma Control in Treated Patients with Asthma" J. Allergy Clin Immunol, 2006, vol. 118, No. 6, pp. 1226-1233.

Bandi V., et al., "Nontypeable Haemophilus Influenzae in the Lower Respiratory Tract of Patients with Chronic Bronchitis", American Journal of Respiratory and Critical Care Medicine, 2001, 164: 2114-2119.

Nagayama Y., et al., "Bacterial Colonization in Respiratory Secretions from Acute and Recurrent Wheezing Infants and Children", Pediatr. Allergy Immunol., 2007, 18: 110-117.

(56) References Cited

OTHER PUBLICATIONS

Nahm D-H., et al., "Elevation of Specific Immunoglobulin A Antibodies to Both Allergen and Bacterial Antigen in Induced Sputum from Asthmatics", Eur. Respir. J., 1998, 12:540-545.
Patrick D.M., et al., "Sever Exacerbations of COPD and Asthma, Incremental Benefit of Adding Ipratropium to Usual Therapy", Chest, Aug. 1990, 98: 297-298.
Fokkens W.J., et al., "European Position Paper on Nasal Polyps 2007", Rhinology 45: suppl. 20: 1-139.
Simpson J.L., et al., "Inflammatory Subtypes in Asthma: Assesment and Identification Using Induced Sputum", Respirology, 2006, 11: 54-61.
Stenius-Aarmiala B., et al., "Lack of Clinical Exacerbations in Adults with Chronic Asthma After Immunization with Killed Influenzae Virus" Chest, 1986, 89: 786-789.
Wenzel S., "Asthma: Defining of the Persistent Adult Phenotypes" Lancet, 2006, 368: 804-813.
Notification of Reasons for Rejection dated Nov. 26, 2013, by the Japanese Patent Office, for corresponding Patent Application No. JP 2011-526594.
KYD and Cripps, "Nontypeable Haemophilus influenzae: challenges in developing a vaccine", Journal of Biotechnology, 1999, pp. 103-108, vol. 73, Elsevier Science B.V.
Fourth Examination Report dated Oct. 15, 2013, mailed by the Australian Patent Office, for corresponding Patent Application No. AU 2009294321.

\* cited by examiner

Distribution of Bacterial Isolates in Sputum

| Study drug | N pts with positive culture & N pts with N different isolates | Total No. positive samples | No. sputum samples bacteriology positive / No. pts with positive bacterial isolates after Visit 1 | | | | |
|---|---|---|---|---|---|---|---|
| | | | H influenzae | M catarrhalis | S pneumoniae | P aeruginosa | P species |
| HI-164OV | 27<br>1P-15<br>2P-7<br>3P-5 | 110 | 64/20 | 11/11 | 11/7 | 24/7 | 0/0 |
| Placebo | 33<br>1P-18<br>2P-9<br>3P-3<br>4P-3 | 144 | 72/23 | 16/8 | 13/9 | 42/16 | 1/1 |

Figure 11

Distribution of Bacterial Isolates in Sputum (COPD Subgroup)

| Study drug | N pts with positive culture & N pts with N different isolates | Total No. positive samples | No. sputum samples bacteriology positive / No. pts with positive bacterial isolates after Visit 1 | | | | |
|---|---|---|---|---|---|---|---|
| | | | H influenzae | M catarrhalis | S pneumoniae | P aeruginosa | P species |
| HI-164OV | 13<br>1P-7<br>2P-4<br>3P-2 | 45 | 23/8 | 7/7 | 6/4 | 9/3 | 0/0 |
| Placebo | 19<br>1P-9<br>2P-6<br>3P-2<br>4P-2 | 88 | 39/14 | 12/5 | 10/6 | 26/11 | 1/1 |

Figure 12

| Increase of stimulation index in Blood T-cells proliferation following administration of vaccines | | |
|---|---|---|
| | Week 28-34 | Week 56-62 |
| Broncostat™ vaccine (as described in PCT Patent Application No. WO86/05691) | 10% (not a statistically significant result) | 40% (not a statistically significant result) |
| HI-164OV vaccine | 100% ($P=0.001$ therefore a statistically significant result) | 110% ($P=0.002$ therefore a statistically significant result) |

Figure 13

ASTHMA AS A SPECTRUM OF AIRWAYS DISEASE

NON-TYPEABLE *HAEMOPHILUS INFLUENZAE* VACCINES AND THEIR USES

This application is a National Stage under 35 U.S.C. § 371 of PCT International Application No. PCT/IB09/007303, filed Sep. 17, 2009, which was published in English on Mar. 25, 2010 as WO 2010/032141 under PCT Article 21(2), which claims the benefit of U.S. Provisional application No. 61/097,729, filed on Sep. 17, 2008, all of which are hereby incorporate herein by reference in their entireties.

TECHNICAL FIELD

The present application relates to non-typeable *Haemophilus influenzae* vaccines and their uses for the treatment of pulmonary diseases such as chronic obstructive pulmonary disease and asthma. The present application also relates to novel strains of *Haemophilus influenzae* useful for treating pulmonary diseases such as chronic obstructive pulmonary disease and asthma.

BACKGROUND

Chronic Obstructive Pulmonary Disease (COPD) due largely to the inhalation of tobacco smoke is a major cause of morbidity and mortality being the fourth most common cause of death in the World (Lung Disease Data (2008). American Lung Association). According to estimates by the National Heart, Lung and Blood Institute, in 2007, the annual cost in US for COPD was $42.6 billion, including $26.7 million in direct health care (Lung Disease Data (2008). American Lung Association). The failure of established medical therapy to substantially improve outcome has been disappointing and new management strategies are needed (Global Initiative for COPD (2006). Global Strategy for the Diagnosis, Management & Prevention of COPD, which can be found on the web site of the Global Initiative for Chronic Obstructive Lung Disease). The underlying pathology of COPD includes a narrowing of the small airways and destruction of lung parenchyma, outcomes that at least in part are a consequence of an inflammatory process. Recurrent acute exacerbations are linked to worsening of airflow obstruction and health status possibly because they reflect more intense intrabronchial inflammation. The cause of this inflammatory response is complex, but in part includes bacterial colonization of the intrapulmonary bronchus mucosa which has been damaged by inhalation of toxic material (Sethi, 2006, Chest 129:223-224).

Acute exacerbations are critical events in the natural history of COPD and are more common in severe disease. Acute exacerbations reduce quality of life, accelerate further decline in lung function, and are major determinants of hospitalization and death (Global Initiative for COPD, 2006; Niewoehner, 2006, Am. J. Med. 119(10 Suppl. 1):38-45; Wedzicha & Seemungal, 2007, Lancet 370(9589):786-96; Sethi, 2006, Chest 129:223-224; Anzueto, 2007, Clin. Chest Med. 28(3):609-16, vii; and Look et al., 2006, Proc. Am. Thorac. Soc. 3(6):482-3). Once patients are hospitalized with an exacerbation they remain at high risk of hospital readmission or death (Sin & Tu, 2001, Am. J. Respir. Crit. Care Med. 164(4):580-4).

Prevention of COPD exacerbations is a major goal of management (Global Initiative for COPD Guidelines, 2002; Celli & MacNee, 2004, Eur. Respir. J. 23(6):932-46; O'Donnell et al., 2007, Can. Respir J. 14 Suppl. B:5B-32B), with prevention or reduction in the number of exacerbations likely having beneficial effects on the long-term clinical course of the disease and patients' quality of life (Burge et al., 2000, BMJ 320(7245):1297-303; Calverley et al., 2003, Chest 124(4):1350-6; Vincken et al., 2002, Eur. Respir. J. 19(2):209-16; and Casaburi et al., 2002, Eur. Respir J. 19(2):217-24).

Asthma is a chronic inflammatory condition of the airways characterized by reversible airway obstruction, and has traditionally been classified as extrinsic (due to allergic reaction to inhaled allergens such as pollens and house dust mite) or intrinsic (not due to classical allergy), the mechanism for which is unknown. Extrinsic asthma is also referred to as "allergic" asthma, whereas intrinsic asthma is also referred to as "non-allergic" or "idiopathic" asthma.

In contrast to COPD, asthma is a typically chronic condition involving the respiratory system in which the airways occasionally constrict, become inflamed, and are lined with excessive amounts of mucus, often in response to one or more triggers. These episodes may be triggered by such things as exposure to an environmental stimulant such as an allergen, environmental tobacco smoke, cold or warm air, perfume, pet dander, moist air, exercise or exertion, or emotional stress. In children, the most common triggers are viral illnesses such as those that cause the common cold. This airway narrowing causes symptoms such as wheezing, shortness of breath, chest tightness, and coughing. The airway constriction responds to bronchodilators. Between episodes, most patients feel well but can have mild symptoms and they may remain short of breath after exercise for longer periods of time than the unaffected individual. The symptoms of asthma, which can range from mild to life threatening, can usually be controlled with a combination of drugs and environmental changes.

In a recently reported study based on diagnosed asthma subjects, asthma was classified based on differences in eosinophil and neutrophil counts in sputum (Simpson et al., 2006, Respirology 11:54-61). The subjects in the study were divided into different asthma subtypes based on the presence of these cell types compared to healthy control subjects. Several asthma sub-types were identified including neutrophilic asthma (>61% neutrophils) and eosinophilic asthma (>1.01% eosinophils). The neutrophilic asthma group comprised approximately 20% of the overall number of asthmatics. The study further reported persistent neutrophilia in the majority of these subjects over both short term (4 week) and long term (mean 5.3 years) intervals between sampling despite no subject reporting respiratory tract infection during the month prior to assessment. While subjects with asthma were found to have higher levels of intracellular bacteria and macrophages than healthy controls, no significant differences were found between neutrophilic asthmatics and the other asthma groups. Indeed, the levels of bacteria found were stated to be less than that consistent with acute bacterial infections, and the report concluded there was no evidence of bacterial infection to explain the inflammatory process of neutrophilic asthma.

Bronchitis is an inflammation of the bronchi (medium-size airways) in the lungs. Chronic bronchitis (CB) is not necessarily caused by infection and is generally part of COPD syndrome. CB is defined clinically as a persistent cough that produces sputum (phlegm) and mucus, for at least three months in two consecutive years.

Non-typeable *Haemophilus influenzae* (NTHi) is the most common pathogenic bacteria associated with chronic bronchitis (CB) (Sethi and Murphy, 2001, Clin. Microbiol. Rev. 14:336-363). NTHi can be found in the upper airways (e.g., nose, middle ear, throat and sinuses) of healthy patients and patients with CB (Sethi and Murphy, 2001, Clin. Microbiol. Rev. 14:336-363) as well as several locations of the respiratory tract, including the lumen, adhering to mucosal epithelial cells in the interstitium of the submucosa (Moller et al., 1998, Am. J. Respir. Crit. Care Med. 157:950-56). Studies of non-obstructive and obstructive CB have observed that a large proportion of patients have persistent infection with NTHi (Murphy et al., 2004, Am. J. Respir. Crit. Care Med. 170:266-72).

FIG. 4 is a side perspective view of the rim cover of FIG. 1 engaged with the rim of a wheel, the view is of the side of the wheel adjacent the vehicle;

Both NTHi and *Staphylococcus aureus* have previously been shown to induce non IgE mediated and enhanced IgE-mediated histamine release from mast cells obtained by broncheoalveolar lavage from the airways of patients with CB. In the case of NTHi, it has been reported that exotoxin may be responsible for the enhancement of IgE mediated histamine release (Clementsen et al., 1990, Allergy 45: 10-17) Immune cells isolated from patients with CB during acute exacerbations have been shown to be both sensitized and hyperactive to the patient's own bacteria (Norn et al., 1994, Agents Actions 41, Special Conference Issue 1994: C22-C23). Several studies have also reported specific IgE antibodies produced in response to respiratory infection by fungi (e.g., *Aspergillus*) and viruses (e.g., respiratory syncytial virus, parainfluenza virus (Welliver et al., 1982, J. Pediatrics 101:889-96)) and bacteria (*S. pneumoniae* (Kjaergard et al., 1996, APMIS 104:61-67; Tee and Pepys, 1982, Clin. Allergy 12:439-50; Pauwels et al., 1980, Allergy 157:665-9), *S. aureus* (Rhode et al., 2004, Respir. Med. 98:858-64; Tee and Pepys, 1982, Clin. Allergy 12:439-50), *Pseudomonas aeruginosa* (Shen et al., 1981, Infect. Immun. 32:967-68), and *Mycoplasma pneumoniae* (Seggev et al., 1996, Ann. Allergy Asthma Immunol. 77:67-73). IgE antibodies specific for NTHi have also been identified in the serum of patients with CB (Kjaergard et al., 1996, APMIS 104; 61-67; Tee and Pepys, 1982, Clin. Allergy 12:439-50) and cystic fibrosis (Tee and Pepys, 1982, Clin. Allergy 12:439-50).

In a study of patients with bronchial asthma, IgE antibodies to NTHi were found in 29% of patients. Antibodies to NTHi and/or *Streptococcus pneumoniae* were also present in 22% of patients with no other IgE mediated hypersensitivity. However, higher levels of IgE bacterial antibodies were found in patients with demonstrable IgE antibodies to various inhalant antigens (suggesting an allergic phenotype) (Pauwels et al., 1980, Allergy 157:665-9). While it has been hypothesized that bacterial infections may play a role in the induction and exacerbation of extrinsic asthma, it has been considered that exacerbation of asthma is predominantly triggered by viral infection. Indeed, the clinical effect of bacterial vaccines in the treatment of asthma has been questioned, leading to international World Health Organization (WHO) recommendations that bacterial vaccines have no role in modern asthma treatment.

Despite massive amounts of research focused on therapeutic asthma intervention and treatment, the condition remains a major, costly and growing problem in modern Westernized societies.

Citation or identification of any reference in this application shall not be construed as an admission that such reference is available as prior art to the present application.

SUMMARY

A novel form of immunotherapy was developed, which involved the oral administration of inactivated non-typeable *Haemophilus influenzae* (NTHi), to stimulate the common mucosal system. Protection against acute exacerbations in COPD was associated with reduction in density of NTHi within sputum. These early studies used a poorly characterized NTHi isolate. A combination of selection assays was used to identify one NTHi isolate (which, unless otherwise indicated, is referred to interchangeably herein as NTHi164, HI-164, isolate 164 or strain 164) that induced broad cross-protection.

Applicants have additionally surprisingly discovered that vaccination with HI-164 is useful for treating asthma and reduces the need for anti-asthma therapy.

Accordingly, the present application is directed to vaccines containing HI-164 and similar strains of NTHi, and their uses to treat diseases involving acute episodes of colonization of the mucosal system, such as the mucosal system of the lower airways. The present application is also directed to vaccines containing HI-164 and similar strains of NTHi, and their uses to treat pulmonary diseases such as asthma, COPD, and chronic bronchitis that is not associated with COPD. In certain embodiments, the vaccine is a monobacterial vaccine comprising one or more strains NTHi and/or one or more immunogenic fractions of said species of NTHi.

The NTHi strains useful in the vaccines of the present application are characterized by a combination of any (e.g., two, three, four, five, six or all) of the following characteristics:

(1) Lacks a B capsule gene;
(2) Is biotype I;
(3) Lacks a beta-lactamase gene;
(4) Grows aerobically;
(5) Is capable of eliciting a mucosal *Haemophilus influenzae*—specific IgA response, as reflected by an at least 10%, at least 20%, at least 50%, at least 70%, at least 100%, or other statistically significant increase in *Haemophilus influenzae*—specific IgA in the saliva;
(6) Is capable of stimulating *Haemophilus influenzae*-specific T cells in Peyer's patches, as reflected by an at least 10%, at least 20%, at least 50%, at least 70%, at least 100%, or other statistically significant increase in lymphokine production by T-cells from Peyer's patches in response to exposure to *Haemophilus influenzae*);
(7) Encodes an outer membrane protein 2 that displays at least 90%, at least 95%, at least 98%, at least 99%, at least 99.5%, or 100% sequence identity with the outer membrane 2 protein of NTHi-164;
(8) Encodes an outer membrane protein 26 that displays at least 90%, at least 95%, at least 98%, at least 99%, at least 99.5%, or 100% sequence identity with the outer membrane 26 protein of NTHi-164;
(9) Expresses an outer membrane protein 2 that runs as a doublet on single dimensional polyacrylamide gel electrophoresis;
(10) Expresses an outer membrane protein 2 that has a pI of 9.1-9.3, most preferably a pI of 9.2;
(11) Expresses prominently on a two-dimensional gel of a whole cell extract at least five, at least 10 or at least 15 of the proteins listed in Table 11A;
(12) Expresses prominently on a two-dimensional gel of a whole cell extract at least two or at least three of the proteins listed in Table 11B;
(13) Expresses prominently on a two-dimensional gel of a whole cell extract at least three, at least four, at least five, at least seven or at least ten of the proteins listed in Table 11A, but not listed in Table 11C;

(14) Expresses prominently on a two-dimensional gel of a whole cell extract at least three, at least four, or at least five of the proteins listed in Table 11A and Table 11D.

As used herein, the term "expresses a protein prominently on a two-dimensional gel" indicates that the protein is present in a spot sufficient for extraction and MALDI analysis on a two-dimensional gel.

Additionally, the present application provides therapeutic regimens for COPD patients and asthma patients.

In certain embodiments, the therapeutic regimens for asthma comprise (1) testing a patient, for example a patient who exhibits symptoms of asthma, for (a) an elevated neutrophil level in saliva, (b) the presence of a microorganism in sputum or saliva, and/or (c) antibodies specific for the NTHi and (2) administering a vaccine of the present application to a patient who tests positive for one, two or all three parameters. In certain embodiments, the vaccine administered comprises one, two or more NTHi strains of the present application and/or an immunogenic fraction of NTHi strains of the present application.

The vaccine of the present application may be a polyvalent vaccine or, more preferably, a monobacterial vaccine.

In certain embodiments, the vaccine of the present application may be in the form of a tablet, said tablet comprises a core containing said population or said membrane fraction and an enteric coating surrounding said core.

In the vaccine of the present application the weight of the core is 400 mg to 500 mg.

In the vaccine of the present application killed bacteria or membrane fraction constitutes 7.5% to 15% of the weight of the core of said tablet.

In the vaccine of the present application killed bacteria or membrane fraction constitutes approximately 10% of said core of said tablet.

In the vaccine of the present application said subenteric coating results in a 2% to 3% of the weight of the core.

In the vaccine of the present application said enteric coating results in a 10% to 12% of the weight of the core.

Any discussion of documents, acts, materials, devices, articles or the like that has been included in this specification is solely for the purpose of providing a context for the present application. It is not to be taken as an admission that any or all of these matters form part of the prior art base or were common general knowledge in the field relevant to the present application as it existed anywhere before the priority date of this application.

The features and advantages of the present application will become further apparent from the following detailed description of embodiments thereof.

BRIEF DESCRIPTION OF THE FIGURES

FIG. 5A demonstrates peripheral blood lymphocyte proliferation to 1 µg HI-164 antigen in vitro. FIG. 5B shows peripheral blood lymphocyte proliferation to 10 µg HI-164 antigen in vitro. FIG. 5C shows peripheral blood lymphocyte proliferation to PHA in vitro.

FIG. 11 is a table of total bacterial isolates in sputum following immunization with HI-1640V as compared to immunization with placebo.

FIG. 12 is a table of specific bacterial isolates in sputum following immunization with HI-1640V as compared to immunization with placebo.

FIG. 13 depicts a comparison of the efficacy of HI-1640V as compared to the product BRONCOSTAT™ (described in PCT Application No. WO86/05691, is a *Haemophilus Influenzae* Killed Cells vaccine).

FIG. 16A. HI-164, Plate grown prep 2. FIG. 16B. HI-166, Plate grown prep 1. FIG. 16C. HI-167, Plate grown prep 1. FIG. 16D. HI-164, Outer membrane protein (OMP) preparation.

DETAILED DESCRIPTION

The present application provides NTHi-based vaccines for the treatment of pulmonary diseases such as asthma and COPD.

The patient needs not have an NTHi infection to benefit from the vaccines of the present application. Thus, in certain aspects, a patient to whom a vaccine of the present application is administered does not have an NTHi infection or markers indicative of an NTHi infection (e.g., NTHi-specific antibodies). In other aspects, the patient is positive for an NTHi infection or has markers indicative of an NTHi infection.

Because, in certain embodiments, a vaccine of the present application is capable of eliciting a non-specific immune response against bacteria other than NTHi, a patient may be positive for bacteria other than NTHi infection or has markers indicative of infection by bacteria other than NTHi. In specific embodiments, the bacteria is one or more of: *Staphylococcus aureus*; a typeable strain of *Haemophilus influenzae*; *Streptococcus pneumoniae*; *Escherichia coli*; *Pseudomonas aeruginosa*; *Mycoplasma pneumoniae*; *Haemophilus parainfluenzae*; β-Haemolytic *Streptococcus* spp.; α-Haemolytic *Streptococcus* spp.; *Pseudomonas* spp.; *Klebsiella pneumoniae*; *Serratia marcescens*; *Enterobacter cloacae*; *Chlamydia pneumoniae*; and *Moraxella catarrhalis*.

The patient to whom the vaccine is administered in accordance with the present application will normally be a human being although the vaccine may also be administered to any suitable mammalian asthma model.

Additional and alternative parameters for a patient to whom the vaccine of the present application is administered are discussed below.

Figure 17:
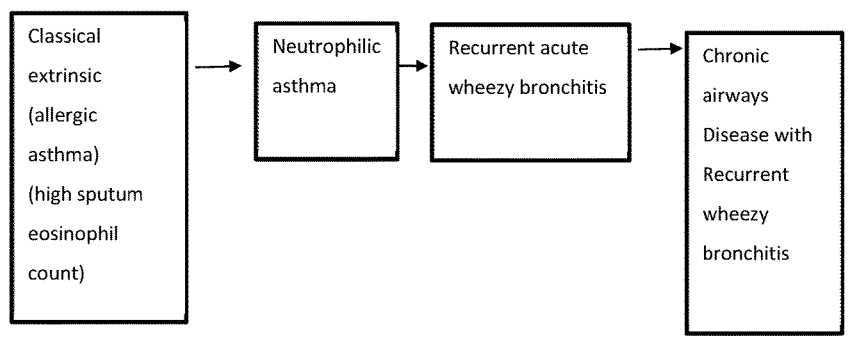
FIG. 17 provides a view of asthma as a spectrum of airways disease.

Conventionally in asthma studies, care has been taken to study discrete groups and generally, subjects with clearly defined asthma (e.g., classical extrinsic asthma) are separated from other groups (e.g., those with smoking-related airways disease) leading to the studies being conducted on defined groups of asthmatics in isolation of other groups of asthmatics. However, this is an artificial categorization and rather, it is more realistic to view asthma as a spectrum of airways disease as illustrated in FIG. 17.

Various different observations have been made with respect to these different clinical manifestations of asthma. In brief, these can be summarized as follows:

The induction of IgE antibody to inhaled antigens (e.g., pollens) gives rise to classical allergic asthma in which allergen-specific IgE binds to mast cells causing degranulation of the mast cells and releasing of mediators such as histamine that give rise to allergic symptoms.

Colonization of damaged airways and intermittent viral infection can lead to neutrophil flux into the bronchus (acute bronchitis) (usually associated with wheeze—thought to follow "inflammation" of the bronchus).

Smoking leading to lung damage can render the subject prone to infection of the airways.

However, many asthma subjects with clinically diagnosed asthma are 'mixed' with respect to these components and it is proposed that this spectrum of asthma disease can be reconciled by recognition that different pathogenic pathways can lead to asthma and that these pathways can co-exist. In particular, without being limited by theory, it is thought by the applicants that the dominant cause of wheeze in many asthmatics without demonstrable classical allergen hypersensitivity (e.g., negative tests for IgE antibody to house dust, pollens and the like, and/or whom have elevated eosinophil counts) is due to an IgE antibody mediated reaction to colonizing and/or recurrent exposure microorganisms in conjunction with the ability of the microorganism to induce and activate neutrophils. Specifically, microorganism-based vaccines can reduce the load of the corresponding microorganism to the small airways, and provide effective treatment for so-called "intrinsic asthma".

In other aspects, and also without being limited by theory, it is thought that some patients who are amenable to treatment by the vaccines of the present application are allergic to bacteria and have IgE antibodies. It is also believed that in such individuals interactions may exist between bacteria and state of allergy to other allergens that contribute to the asthmatic state. Thus, in certain aspects, the vaccines of the present application are used to treat a patient who is an allergic asthmatic.

More broadly, benefit from the vaccines of the present application can be derived by those patients exhibiting one or more parameters indicative of exposure to a microorganism that is capable of colonizing the airways, such as elevated neutrophil levels (with or without elevated eosinophil levels) in saliva, current infection with the microorganism as for instance indicated by the presence of the microorganism in sputum or saliva and/or antibodies specific to the microorganism, and those patients with damaged airways such as arising from smoking (chronic pulmonary obstructive disease (COPD)) or chronic bronchitis (particularly those patients with wheeze). It is recognized, for instance, that patients with damaged airways are highly prone to infection/colonization by pathogenic microorganisms. While damage to airways classically follows smoking, extrinsic asthma can also damage the airways (hence, later onset of cough and sputum associated with airways infection). Benefit may also occur in asthmatic patients with combined mechanisms (e.g., atopic subjects with IgE antibody to a microorganism that colonizes the airways), and the treatment of asthma and asthma symptoms in general as a result of decrease or avoidance of induction of IgE production resulting from exposure to a vaccine targeting the microorganism.

Antibody levels can be measured in blood, serum, plasma, sputum or saliva samples using any suitable conventionally known assay protocol including, enzyme linked immunosorbent assay (ELISA) or other immunoassay. The antibody tested for can be selected from one or more of IgA, IgM, IgG and IgE, and subclasses thereof, such as IgG1 and/or IgG3. Total IgE and/or IgE antibody specific to a microorganism that colonizes the airways will generally be measured in sputum or saliva sample. Neutrophil levels can also be measured in saliva or sputum using any appropriate conventionally known assay including microscopic evaluation following cell staining. Similarly, any suitable method known in the art can be employed to determine microorganism counts/level of infection. Antibody levels, neutrophil levels and NTHi counts can be compared against corresponding reference level(s) derived from classical extrinsic asthmatics (e.g., exhibiting eosinophilic and/or hyper-responsiveness) or for example, a non-asthmatic control or other suitable reference group. Statistical Methods for differentiating asthma groups are described in, for instance, Simpson et al., 2006, Respirology 11:54-61.

In certain aspects, patients to whom the vaccines of the present application are administered may or may not have COPD and/or symptoms associated with COPD such as chronic bronchitis and emphysema.

COPD is a slowly progressive disease of the airways that is characterized by the gradual loss of lung function. Patients with COPD, which includes chronic bronchitis and emphysema, often require emergency treatment and sometimes hospitalizations during periods of exacerbations of their disease. COPD leads to chronic airflow obstruction, which is defined as a persistent decrease in the rate of airflow through the lungs when the person breathes out (exhales). Symptoms such as wheezing and shortness of breath are relieved when airflow obstruction decreases by reversing bronchial smooth muscle spasm, inflammation, and increased secretions.

Thus, in certain aspects, a patient to whom a vaccine of the present application is administered may have one or more of the following symptoms: chronic bronchitis, emphysema, chronic cough, excessive sputum production, low blood oxygen levels, severe disabling shortness of breath, reduced airflow through the lungs, bronchial smooth muscle spasm, bronchial inflammation, and bronchial increased secretions (including mucus plugs).

Severe COPD is generally categorized into two stereotypes—the pink puffer and the blue bloater. Most advanced COPD patients have features of both stereotypes. The pink puffer is typically an asthmatic, barrel-chested emphysematous patient who exhibits pursed-lip breathing and has no cyanosis or edema. Usually, such a patient uses extrathoracic muscles to breathe, produces minimal sputum, and experiences little fluctuation in the day-to-day level of dyspnea. Diaphragmatic excursions are reduced, and breath and heart sounds are distant. The barrel-shaped chest is non-specific because elderly persons commonly have increased lung compliance and larger resting lung volumes. The blue bloater is typically overweight, cyanotic, and edematous and has a chronic productive cough. Elderly blue bloaters are uncommon because blue bloaters often have cor pulmonale, which rapidly leads to death if not treated appropriately. In certain aspects, a patient to whom the vaccines of the present application are administered exhibit the characteristic of a pink puffer and/or a blue bloater.

Chronic hypoxia (reduction of oxygen supply to the body despite adequate blood flow through the body), hypertension, and left ventricular hypertrophy are related conditions which may be symptomatic of COPD or coincident with COPD. Thus, in certain aspects, a patient to whom a vaccine of the present application is administered has chronic hypoxia, hypertension and/or left ventricular hypertrophy.

Cystic fibrosis is an example of an obstructive lung disorder that results in bronchiectasis and progressive declines in lung capacity. Thus, in certain aspects, a patient to whom a vaccine of the present application is administered may have cystic fibrosis.

In certain aspects, the patient is positive for a gene or other marker associated with COPD (see, e.g., US 20080108079 A1 and US 20080044843 A1, respectively, each of which is incorporated herein by reference in its entirety). The patient positive for one or more genes or markers may or may not display symptoms of COPD; i.e., the vaccines of the present applications may be administered prior to or following onset of COPD symptoms.

In certain aspects, the patient to whom the vaccines of the present application are administered does not have asthma. In a specific embodiment, the patient does not have extrinsic asthma. In another specific embodiment, the patient does not have intrinsic asthma.

According to the present application, treatment of asthma encompasses the treatment of patients already diagnosed as having any form of asthma at any clinical stage or manifestation; the delay of the onset or evolution or aggravation or deterioration of the symptoms or signs of asthma; preventing and/or reducing the severity of nighttime and/or daytime asthma attacks; improving lung capacity; preventing a reduction in lung capacity of asthmatic patients; preventing or limiting adverse exacerbations; preventing or limiting hospital admissions from asthma symptoms; and/or reducing or limiting the need for antibiotics, steroids, bronchodilators or other medications.

Advantageously, administration of a vaccine in accordance with one or more embodiments of the present application can lead to a reduction in IgE antibodies and/or a reduction in the symptoms or severity of the asthma (e.g., intrinsic or neutrophilic asthma) in the patient.

According to the present application, treatment of COPD encompasses the treatment of patients already diagnosed as having any form of COPD at any clinical stage or manifestation; the delay of the onset or evolution or aggravation or deterioration of the symptoms or signs of COPD; preventing and/or reducing the severity of episodes of wheezing and/or shortness of broth; improving lung capacity; preventing a reduction in lung capacity patients; preventing or limiting adverse exacerbations; preventing or limiting hospital admissions from COPD symptoms; and/or reducing or limiting the need for antibiotics, steroids, bronchodilators or other medications.

The vaccine can be administered in accordance with any regimen suitable for generating an effective immune response against a microorganism infection. The vaccine of the present application can be administered as a single dose or, where desired or necessary, the initial dose can be followed by boosters at several days, several weeks, or several months or years following the initial dose.

In an exemplary embodiment, a single dose of the vaccine can be administered once per year pre-winter. Optionally, one or more "booster" doses of the vaccine administered at an interval of a number of weeks or months may also be given. Alternatively, a number of doses of the vaccine may be administered over the course of a number of weeks in order to generate an effective immune response against infection and/or colonization by a microorganism that is capable of colonizing the airways such as NTHi.

Each dosage administered to a patient can consist of one unit dose (as described below), or more or less. The specific dosage mounts effective for therapeutic use will depend on, e.g., the immunogenic component of the vaccine (as described below), the weight and general state of health of the patient, the judgment of the prescribing physician, and the proposed mode of delivery and nature of the vaccine (e.g., capsule, powder, liquid, aerosol delivery, tablets, enterically coated tablets etc.).

The vaccines of the present application may be administered using any desired route of administration, including but not limited to, e.g., subcutaneously, intravenously, intramuscularly or intradermally, although mucosal administration is preferred. Mucosal routes of administration include, but are not limited to, oral, rectal and nasal administration. Preparations for mucosal administrations are suitable in various formulations as described below. The route of administration can be varied during a course of treatment.

The vaccine utilized in a method of the present application will typically contain whole killed or inactivated (e.g., attenuated) NTHi isolate(s) (e.g., formalin-killed) according to the present application. However, soluble or particulate antigen comprising or consisting of outer cell membrane and/or surface antigens of the microorganism can be utilized as well, or instead of, whole killed NTHi.

Soluble and/or particulate antigen can be prepared by disrupting killed or viable selected NTHi isolate(s). A fraction for use in the vaccine can then be prepared by centrifugation, filtration and/or other appropriate techniques known in the art. Any method which achieves the required level of cellular disruption can be employed including sonication or dissolution utilizing appropriate surfactants and agitation, and combination of such techniques. When sonication is employed, the isolate can be subjected to a number of sonication steps in order to obtain the required degree of cellular disruption or generation of soluble and/or particulate matter of a specific size or size range.

In specific embodiments, the immunogenic components are killed cells and/or an immunogenic fraction of NTHi species of the present application.

The lack of a beta-lactamase gene is an optional feature of the NTHi strains of the present application. Beta-lactamases are enzymes produced by some bacteria and are responsible for their resistance to beta-lactam antibiotics like penicillins, cephalosporins, cephamycins, ertapenems and carbapenems. Beta-lactam antibiotics are typically used to treat a broad spectrum of gram positive and gram-negative bacteria. Because beta-lactamase expression may result in antibiotic resistance, the presence of a beta-lactamase gene is generally not preferred during the manufacture and administration of killed pathogens such as NTHi. The lack of a beta-lactamase gene allows the organism to be controlled with beta-lactam antibiotics should the need arise during manufacturing or an adverse event in a patient.

The non-typeable *H. influenzae* isolate HI-164, deposited under the provisions of the Budapest Treaty with the National Measurement Institute in Melbourne, Australia as of Aug. 13, 2008 and assigned accession no. V08/021002, as is particularly suitable for use in vaccines of the present application. Another suitable strain is non-typeable *H. influenzae* isolate HI-167, deposited under the provisions of the Budapest Treaty with the National Measurement Institute in Melbourne, Australia as of Aug. 13, 2008 and assigned accession no. V08/021003.

In one or more embodiments, the outer cellular membrane fraction or membrane protein(s) of the selected NTHi strain(s) will be utilized as the immunogenic component of a vaccine of the present application.

Immunogenic proteins and peptides of NTHi have been described. In a specific embodiment, an NTHi outer membrane protein ("OMP") fraction or OMP protein is used as an immunogenic component of a vaccine of the present application. NTHi OMPs include OMP P6, a highly conserved 16-kDa lipoprotein (Nelson et al., 1988, Infect. Immun. 56:128-134) that is a target of human bactericidal antibody and induces protection both in humans and in animal models. In chronic pulmonary obstructive disease (COPD), OMP P6 has been shown to evoke a lymphocyte proliferative response that is associated with relative protection from NTHi infection (Abe et al., 2002, Am. J. Respir. Crit. Care Med. 165: 967-71). Accordingly, OMP P6 or any other suitable outer membrane NTHi proteins, polypeptides (e.g., P2, P4 and P26) or antigenic peptides of such proteins may suitable be used as the immunogenic components of the vaccines of the present application, either in isolated and purified form or as a component of a cellular fraction, such as an OMP fraction.

In a certain aspect, the immunogenic protein or peptide is OMP P26 or an immunogenic fragment thereof. In another aspect, the immunogenic protein or peptide is OMP P2 or an immunogenic fragment thereof. In specific embodiments, the vaccine comprises (1) an OMP P26 protein or immunogenic fragment thereof that has at least 99% or at least 99.5% sequence identity with the OMP P26 protein of NTHi-164, and/or (2) an OMP P2 protein or immunogenic fragment thereof that has at least 99% or at least 99.5% sequence identity with the OMP P2 protein of NTHi-164.

A vaccine of the present application will typically comprise the cells of the selected immunogenic component (i.e., NTHi isolate(s) and/or cellular fractions and/or isolated or purified proteins and/or peptides) in an amount of from about 0.1% to 100% w/w of the vaccine composition, more preferably in an amount of from 1% to 50% of w/w of the vaccine composition.

For whole cell killed vaccines, the unit dose will typically be in a range of from about $10^9$ to about $10^{12}$ killed cells, more preferably from about $10^9$ to about $10^{11}$ killed cells, and most preferably about $10^{10}$ to about $10^{11}$ killed cells.

For vaccines made of cellular fractions of NTHi, the unit dose will be fractionated from about $10^9$ to about $10^{14}$ cells, more preferably fractionated from about $10^{10}$ to about $10^{13}$ cells, and most preferably fractionated about $10^{10}$ to about $10^{12}$ cells.

For vaccines containing isolated or purified proteins and peptide fragments, the unit dose is generally 50-75 mg, 75-100 mg, 100-125 mg, 125-150 mg, 150-175 mg, 175-200 mg or more.

The optimum dosage of the vaccine can be determined by administering different dosages to different groups of test mammals, prior to subsequently infecting the animals in each group with the microorganism, and determining the dosage level required to achieve satisfactory clearance of the pathogen.

A vaccine of the present application may also comprise one or more pharmaceutically acceptable carriers and/or adjuvants. Exemplary adjuvants that may be used are further detailed below. Typically, although not exclusively, the preferred oral vaccine formulation is non-adjuvanted.

Actual methods for preparing the vaccine formulations of the present application will be known or apparent to those skilled in the art and are described in more detail in such publications as Remington's Pharmaceutical Science, 15th ed., Mack Publishing Company, Easton, Pa. (1980).

The vaccines of the present application are generally provided in compositions with pharmaceutically acceptable carriers. Various pharmaceutically acceptable carriers are well known in the art. As used herein, "pharmaceutically acceptable carriers" includes any material which, when combined with an active ingredient of a composition, allows the ingredient to retain biological activity and preferably does not cause disruptive reactions with the subject's immune system.

In general, the vaccines can be prepared in various forms, such as granules, tablets, pills, suppositories, capsules (e.g., adapted for oral delivery), microbeads, microspheres, liposomes, suspensions, salves, lotions and the like. The vaccine itself can be a freeze-dried or lyophilized vaccine reconstituted utilizing a physiologically acceptable buffer or fluid. The vaccine can also contain one or more anti-caking agents, preservatives such as thimerosal or which are otherwise suitable for the proposed mode of administration, stabilizers such as amino acids and sugar moieties, sweetening agents such sucrose, lactose or saccharin, surfactants, pH buffering agents and pH modifiers such sodium hydroxide, hydrochloric acid, monosodium phosphate and/or disodium phosphate, a pharmaceutically acceptable carrier such as physiologically saline, solvents and dispersion media and isotonic preparations.

The vaccine is advantageously presented for oral administration, for example in a lyophilized encapsulated or tabletted form. It is recognized that the immunogenic component of a vaccine of the present application, when administered orally, is preferably protected from digestion. This can be accomplished either by mixing or packaging the immunogenic component in an appropriately resistant carrier, such as a liposome, or within an enteric coating. The preparations may also be provided in controlled release or slow-release forms.

Preferably, the oral formulation is in the form of a capsule or tablet. Such capsules and tablets may be provided with an enteric coating comprising, for example, Eudragate "S" (Trade Mark), Eudragate "L" (Trade Mark), cellulose acetate, cellulose phthalate or hydroxypropylmethyl cellulose. Other carriers suitable for formulating capsules or tablets include binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and wetting agents (e.g., sodium lauryl sulphate). The tablets may be coated by methods well-known in the art. Preparations for oral administration may be suitably formulated to give controlled release of the immunogenic component.

These capsules and tablets may be used as such, or alternatively, the lyophilized material may be reconstituted prior to administration, e.g., as a suspension.

As an alternative to capsules and tablets, the oral vaccine may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

In order to protect the immunogenic component of the vaccine from gastric acidity, a sodium bicarbonate preparation may be advantageously administered before each administration of the vaccine.

The vaccine may also be formulated for administration by inhalation or injection.

Except insofar as any conventional media or agent is incompatible with the immunogenic component of a vaccine of the present application, or the proposed mode of administration, their use the vaccines that can be employed in methods embodied by the present application is specifically encompassed.

Supplementary active agents for boosting the immune response including for instance, probiotic microorganisms, fractions and biological products thereof, and appropriate cytokines, can also be included to the vaccine.

A vaccine of the present application optionally comprises one or more adjuvants. Examples of suitable adjuvants are presented herein below.

Suitable adjuvants include mineral salt adjuvants or mineral salt gel adjuvants. Such mineral salt and mineral salt gel adjuvants include, but are not limited to, aluminum hydroxide (ALHYDROGEL, REHYDRAGEL), aluminum phosphate gel, aluminum hydroxyphosphate (ADJU-PHOS), and calcium phosphate. Other suitable adjuvants include immunostimulatory adjuvant. Such class of adjuvants include, but are not limited to, cytokines (e.g., interleukin-2, interleukin-7, interleukin-12, granulocyte-macrophage colony stimulating factor (GM-CSF), interferon-γ, interleukin-1β (IL-1β), and IL-1 (3 peptide or Sclavo Peptide), cytokine-containing liposomes, triterpenoid glycosides or saponins (e.g., QuilA and QS-21, also sold under the trademark STIMULON, ISCOPREP), Muramyl Dipeptid (MDP) derivatives, such as N-acetyl-muramyl-L-threonyl-D-isoglutamine (Threonyl-MDP, sold under the trademark TERMURTIDE), GMDP, N-acetyl-nor-muramyl-L-alanyl-D-isoglutamine, N-acetyl-muramyl-L-alanyl-D-isoglutaminyl-L-alanine-2-(1'-2'-di-palmitoyl-sn-glycero-3- hydroxyphosphoryloxy)-ethylamine, muramyl tripeptide phosphatidylethanolamine (MTP-PE), unmethylated CpG dinucleotides and oligonucleotides, such as bacterial DNA and fragments thereof, LPS, monophosphoryl Lipid A (3D-MLAsold under the trademark MPL), and polyphosphazenes. Yet other suitable adjuvants include particulate adjuvants, including, but not limited to, emulsions, e.g., Freund's Complete Adjuvant, Freund's Incomplete Adjuvant, squalene or squalane oil-in-water adjuvant formulations, such as SAF and MF59, e.g., prepared with block-copolymers, such as L-121 (polyoxypropylene/polyoxyethylene) sold under the trademark PLURONIC L-121, Liposomes, Virosomes, cochleates, and immune stimulating complex, which is sold under the trademark ISCOM. Yet other suitable adjuvants are microparticulate adjuvants such as, but not limited to, biodegradable and biocompatible polyesters, homo- and copolymers of lactic acid (PLA) and glycolic acid (PGA), poly (lactide-co-glycolides) (PLGA) microparticles, polymers that self-associate into particulates (poloxamer particles), soluble polymers (polyphosphazenes), and virus-like particles (VLPs) such as recombinant protein particulates, e.g., hepatitis B surface antigen (HbsAg).

A preferred class of adjuvants are mucosal adjuvants, including but not limited to heat-labile enterotoxin from *Escherichia coli* (LT), cholera holotoxin (CT) and cholera Toxin B Subunit (CTB) from *Vibrio cholerae*, mutant toxins (e.g., LTK63 and LTR72), microparticles, and polymerized liposomes.

In certain aspects, the adjuvant is an adjuvant that activates a Th1 immune response. Preferably, the adjuvant does not activate a Th2 immune response, although adjuvants that activate a Th2 immune response are within the scope of the present application.

The vaccines of the present application can be formulated in any suitable manner. In general, the vaccines of the present application can be administered orally, nasally, nasopharyngeally, parenterally, enterically, gastrically, topically, transdermally, subcutaneously, intramuscularly, in tablet, solid, powdered, liquid, aerosol form, locally or systemically, with or without added carriers.

A vaccine of the present application can be administered as a capsule or tablet, as a dry powder or in liquid form. Administration can for example be achieved by injection (cg, subcutaneous, or intravenous), orally such as by dosage unit form (e.g., tablet, capsule or dosed liquid form), or by inhalation.

In certain aspects, a vaccine of the present application is administered in a manner that allows the immunogenic component to reach a lymphoid tissue, more preferably a secondary lymphoid tissue, and most preferably a mucosa-associated lymphoid tissue. In certain embodiments, the mucosa-associated lymphoid tissue is BALT (bronchus-associated lymphoid tissue), NALT (nose-associated lymphoid tissue), LALT (larynx-associated lymphoid tissue), or GALT (gut-associated lymphoid tissue). Most preferably, administered by way of an enterically coated tablet to allow delivery of the immunogenic component of the vaccine to Peyer's patches, which are aggregations of lymphoid tissue that are predominantly found in the lowest portion of the ileum, and other gut-associated lymphoid tissue (GALT) in the patient's gut.

Described below are combinatorial methods in which the vaccines of the present application can be utilized. The combinatorial methods of the present application involve the administration of at least two agents to a patient, the first of which is a vaccine targeting a microorganism according to the present application, and the second of which is a second therapeutic agent.

The combinatorial therapy methods of the present application can result in a greater than additive effect, providing therapeutic benefits where neither the vaccine nor second therapeutic agent administered in an amount that is alone effective for treatment of asthma.

In the present methods, the vaccine and the second therapeutic agent can be administered concurrently or successively. As used herein, the vaccine and the second therapeutic agent are said to be administered concurrently if they are administered to the patient on the same day, for example, simultaneously, or 1, 2, 3, 4, 5, 6, 7 or 8 hours apart. In contrast, the vaccine and the second therapeutic agent are said to be administered successively if they are administered to the patient on the different days, for example, the vaccine and the second therapeutic agent can be administered at a 1-day, 2-day or 3-day, one-week, 2-week or monthly intervals. In the methods of the present application, administration of the vaccine can precede or follow administration of the second therapeutic agent.

As a non-limiting example, the vaccine and second therapeutic agent can be administered concurrently for a period of time, followed by a second period of time in which the administration of the vaccine and the second therapeutic agent is alternated.

Because of the potentially synergistic effects of administering a vaccine and a second therapeutic agent, such agents can be administered in amounts that, if one or both of the agents is administered alone, is/are not effective for treating asthma or COPD.

Most people with persistent asthma use a combination of long-term control medications and quick-relief medications, taken with a hand-held inhaler. Asthma symptoms triggered by airborne allergens, such as pollen or pet dander, are also treated with allergy medications.

Accordingly, suitable second therapeutic agents include long-term control medications, quick-relief medications, and allergy medications.

Examples of long-term control medications include, but are not limited to, (1) inhaled corticosteroids such as fluticasone (e.g., Flovent Diskus™), budesonide (e.g., Pulmicort™), triamcinolone (e.g., Azmacort™), flunisolide (e.g., Aerobid™), and beclomethasone (e.g., Qvar™); (2) long-acting beta-2 agonists (LABAs) such as salmeterol (e.g., Serevent Diskus™) and formoterol (e.g., Foradil Aerolizer™, Oxis™, Performist™ and Brovana™); (3) long acting muscarinic antagonists such as tiotropium (e.g., Spiriva™) and ipratropium (e.g., Atrovent™); (4) leukotriene modifiers such as montelukast (e.g., Singulair™), zafirlukast (e.g., Accolate™) and zileuton (e.g., Zyflo CR™); (5) mast cell inhibitors such as cromolyn (e.g., Intal™) and nedocromil (e.g., Tilade™); (7) theophylline Examples of quick-relief medications include (1) short-acting beta-2 agonists (SABAs) such as albuterol or albuterol sulfate (e.g., as sold under brand name Xopenex™ and Ventolin™), (2) short acting muscarinic antagonists, and (3) oral and intravenous corticosteroids such as prednisone, methylprednisolone, mometasone furoate (e.g., as sold under brand name Asmanex™) and ciclesonide (e.g., Aerobid™/Alvesco™).

Examples of allergy medications include (1) immunotherapy, (2) anti-histamines (e.g., Claritin™ and Zyrtec™) and (3) anti-IgE monoclonal antibodies, such as omalizumab (Xolair™). Examples of mucolytics include, but are not limited to, Bronchitol™ (a mannitol inhaler) and Mucomyst™ (an acetylcysteine inhaler).

In certain aspects, the second therapeutic agent itself is a combination product, i.e., a product containing more than one active ingredient. Examples of suitable combination products include Symbicort™ (a combination of formoterol and budesonide); Combivent™ (a combination of atrovent and albuterol); and Advair™ or Seretide™ (a combination of salmeterol and fluticasone); a combination of long acting beta-adrenoceptor agonist such as indacaterol with mometasone; and a combination of long acting beta-2 agonist such as formoterol with mometasone.

BRONCHODILATORS—Medications that help open the airways are a mainstay of treatment for COPD. Bronchodilators are most commonly given in an inhaled form using a metered dose inhaler (MDI), dry powder inhaler (DPI), or nebulizer. It is important to use the inhaler properly to deliver the correct dose of medication to the lungs, rather than the mouth. Any of the bronchodilators described above may be used in combination with the NTHi vaccines of the present application for the treatment of COPD.

VACCINES—In certain aspects, the second therapeutic agent is a vaccine, such as a pneumococcal vaccine, which helps prevent a certain type of pneumonia, or an influenza vaccine, which is generally administered before the influenza season, generally in the late fall or early winter.

ANTIVIRAL AGENTS: For COPD patients who get influenza, antiviral medications may be prescribed. Antiviral medication may also be recommended for people with COPD who have not had an influenza vaccine and are at risk for getting influenza. Thus, in certain aspects, the second therapeutic agent is an antiviral agent.

ANTIBIOTICS—Antibiotics are of some benefit in people with a bacterial respiratory infection who have worsening COPD symptoms. A physician may order a sputum analysis (from sputum in the lungs) to determine if antibiotics are needed in a particular situation. Thus, in certain aspects, the second therapeutic agent is an antibiotic.

OXYGEN—Patients with advanced COPD can have low oxygen levels in the blood. This condition, known as hypoxemia, can occur, even if the person does not feel short of breath or have other symptoms. The oxygen level can be measured with a device placed on the finger (pulse oximeter) or with a blood test (arterial blood gas). Patients with hypoxemia may be placed on oxygen therapy, which can improve survival and quality of life, depending upon the degree to which the oxygen level in the blood was decreased. Thus, in certain aspects, the second therapeutic agent is oxygen.

AUGMENTATION THERAPY FOR SEVERE ALPHA-1-ANTITRYPSIN DEFICIENCY—People with alpha-1-antitrypsin deficiency as a contributor to their COPD can be treated with purified alpha-1-antitrypsin that is prepared from donated, pooled blood. Thus, in certain aspects, the second therapeutic agent is alph-1-antitrypsin.

OTHER THERAPIES—Certain patients with COPD may be given other treatments, including: noninvasive ventilatory support (the use of a special mask and breathing machine to improve symptoms), anti-anxiety or anti-depressant medications, or morphine-like medications to reduce shortness of breath. Such therapies can constitute the second therapeutic agent of the present application.

Example 1: Selection of Non-Typeable *H. influenzae* Strain HI-164

1.1 Background

A number of NTHi isolates, including strain IDs 164, 165, 167 and 168, were collected from 20 patients attending a respiratory clinic at the John Hunter Hospital in Newcastle, Australia. The isolates and another research isolate (strain NTHi-166) were characterized for growth conditions, biotype, serotype, the presence of a B capsule gene and the presence of the beta lactamase gene. The results are given in Table 1 below:

TABLE 1

Growth characteristics of different NTHi isolates

| Strain ID | Growth Condition | Biotype | Serotype | B capsule gene | Beta lactamase |
| --- | --- | --- | --- | --- | --- |
| NTHi-164 | Aerobic | I | Non-typeable | Negative | Negative |
| NTHi-165 | Aerobic | I | Non-typeable | Negative | Positive |
| NTHi-166 | Aerobic | I | Non-typeable | Positive | Negative |

TABLE 1-continued

Growth characteristics of different NTHi isolates

| Strain ID | Growth Condition | Biotype | Serotype | B capsule gene | Beta lactamase |
|---|---|---|---|---|---|
| NTHi-167 | Aerobic | I | Non-typeable | Negative | Negative |
| NTHi-168 | Anaerobic | I | Non-typeable | Negative | Positive |

The isolates were tested for usefulness as the active component of an oral vaccine in a rodent model of acute respiratory infection. The isolates were also tested for ability to stimulate human blood lymphocytes in vitro to secrete IFNγ. On the basis of these tests isolate NTHi-164 has been selected as the NTHi strain for use in the Hunter Immunology Ltd HI-164OV oral vaccine. This isolate has properties that make it an ideal choice for use in an oral vaccine to provide protection against *H. influenzae* infection.

In both the Examples and the remainder of the specification, the term "HI-164OV" refers to a vaccine tablet comprising HI-164, i.e., formalin-killed lyophilized NTHi-164 active substance.

1.2 Summary of Properties of NTHi-164

1.2.1 Microbiological Identification

*H. influenzae* identification: Requires X and V factors for growth. Non-typeable identification (i.e., no capsule of any type) and no expression of B capsule and no gene for B capsule, no β-lactamase.

1.2.2 Growth Characteristics

Grows well in Oxoid™ Tryptone Soya Broth (TSB) supplemented with *Haemophilus* Test (HTM) supplement. Also grows well in Oxoid™ veggitone broth with HTM supplement.

The ability of various media to grow *H. influenzae* NTHi-164 and ATCC19418 was examined and results compared. *H. influenzae* NTHi-164 and *H. influenzae* ATCC19418 were incubated in 250 mL conical flasks containing 100 mL of either Tryptone Soya Broth (Code CM129. Lot B.:301377)

Tryptone Soya Broth (Code CM129. Lot B.:301377) plus Yeast Extract (Oxoid Code L21, Lot Ch-B.:856108)

Veggitone Vegetable Peptone (Oxoid Code VG0100, Lot 335918)

Veggitone Vegetable Peptone (Oxoid Code VG0100, Lot 335918) plus Yeast Extract (Oxoid Code L21, Lot Ch-B.: 856108)

Each medium was supplemented with *Haemophilus* Test Supplement (HTM), Oxoid Code SR158E. Lot B.:312141. Growth was at 37° C. in ambient air with approximately 2 rotations of the flasks per second. The stationary phase was reached after approximately 11 hours of incubation.

All media used supported the growth of both strains of *H. influenzae*, with the more nutritious TSB plus yeast extract and HTM supplement being the preferred formulation. Animal based media (TSB) and vegetable based media (Vegetable Peptone) were approximately equivalent in growth Characteristics for the 2 isolates.

Figure 1:
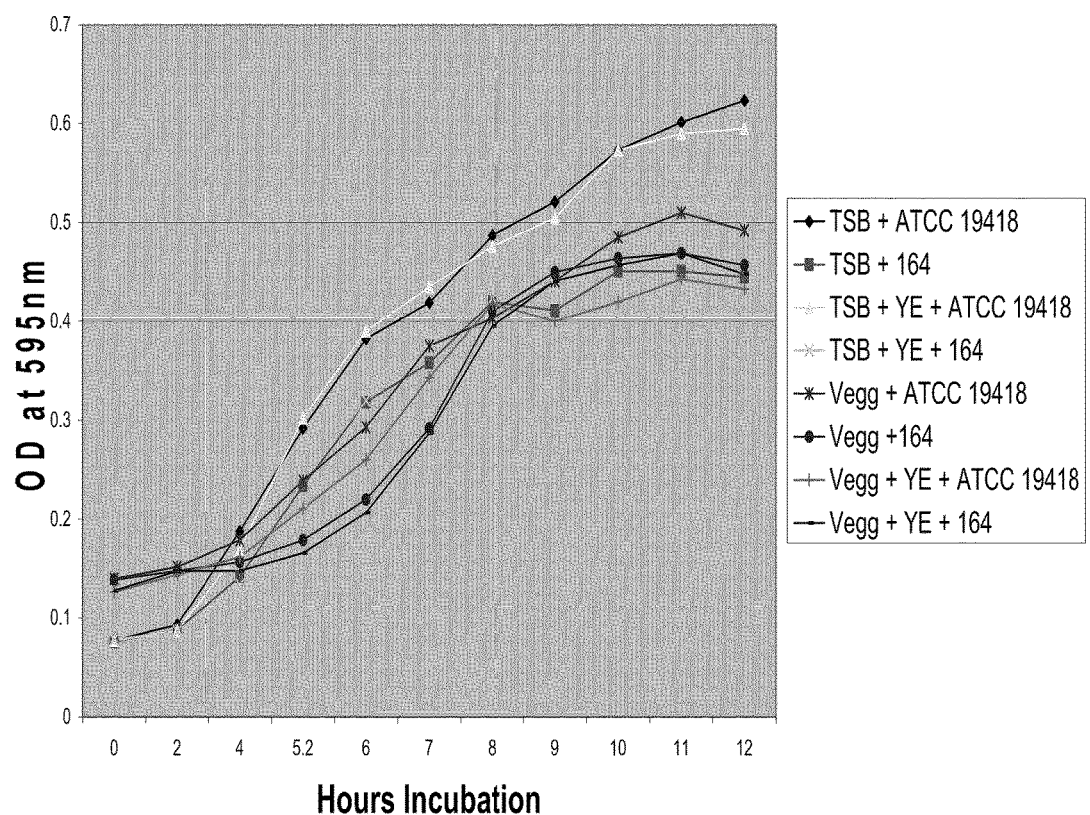
FIG. 1 depicts growth curves NTHi-164 and a reference strain for the various broth media.

With the preferred media formulation (TSB with Yeast Extract and HTM supplement) optical densities for *H. influenzae* strains NTHi-164 and ATCC 19418 plots over time were roughly equivalent, with OD's at 595 nm and 11 hours of incubation for *H. influenzae* NTHi-164 and ATCC 19418 being 0.590 and 0.525 respectively. Please note that other culture media may produce similar or better growth results. Growth curves of NTHi-164 and ATCC 19418 are shown in FIG. 1.

For large scale production, NTHi-164 can be grown in a medium containing 30+/−0.3 g/L tryptone soya broth; 5+/−0.05 g/L yeast extract; and 0.20+/−0.01 g/L antifoam and supplemented with nicotinamide adenine dinucleotide (NAD) at 15 mg/ml and haematin at 15/mg/ml. The supplements are added in volumes of up to 4 mL per L.

1.3 Capacity to Induce Protection in Rodent Models of Infection

These data demonstrate that killed NTHi-164 has the capacity to stimulate a protective immune response. Applicants believe that this capacity is related to the pattern of expression of bacterial antigens and/or existence of natural adjuvants, and/or to the capacity for uptake into Peyer's patches (which is likely related to the particle size and also possibly to adhesion proteins).

1.4 HI-164 Protects Against Acute Respiratory Infection in Rats

Figure 2:
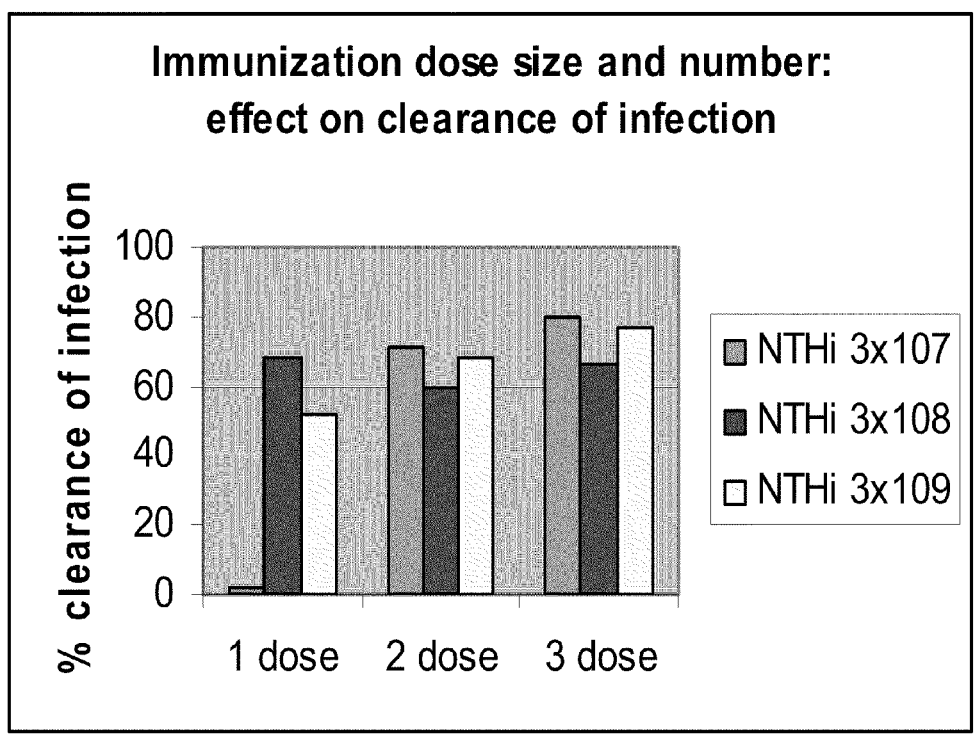
FIG. 2 depicts clearance data of bacteria resulting from different vaccination regimens with NTHi-164 in male Dard Agouti rats.

Rats were immunized on day 0 by a single dose of $3\times10^7$, $3\times10^8$, or $3\times10^9$ formalin-killed NTHi-164 (referred to herein as HI-164) delivered directly to the intestinal lumen, or followed by one oral dose on day 14 or two oral doses on days 14 and 21 (i.e., rats received one, two or three doses). On day 28 a boost dose (with capacity to boost the intestinal dose but without the capacity to provide protective immunity on its own) was delivered to the lungs by instillation into the trachea. Control rats for each immunisation regimen were immunized with placebo (PBS). On day 35 the rats were infected by intra-tracheal instillation of $5\times10^8$ live NTHi-164. Four hours later the rats were killed for sampling. Lungs were lavaged to provide broncho-alveolar lavage (BAL) fluid and the lung was homogenized in PBS to provide a lung homogenate (LH). Serial dilutions of the BAL and LH were prepared and samples of each dilution plated out on chocolate agar plates. The plates were cultured overnight at 37° C. in an atmosphere of 5% $CO_2$. The colonies on the plate were counted and the number of NTHi-164 (colony forming units, or CFU) in the BAL and LH calculated. The total NTHi-164 CFU in the lung was determined. The mean CFU in the lungs for the vaccine immunized and placebo immunized animals was calculated and the clearance of bacteria provided by each vaccination regimen was calculated compared to the relevant control group. The results are shown in FIG. 2. Good bacterial clearance was obtained in animals that received one or more doses when the dose was $3\times10^8$, or $3\times10^9$. Good bacterial clearance was obtained in animals that received two or three doses when the dose was $3\times10^7$.

1.5 NTHi-164 Protects Against *H. influenzae* Respiratory Infection in Mice

These experiments demonstrate the capacity of NTHi-164 to protect mice as well as rats. It further demonstrates that the vaccine is most protective in a mouse strain that is most susceptible to infection.

Figure 3A:
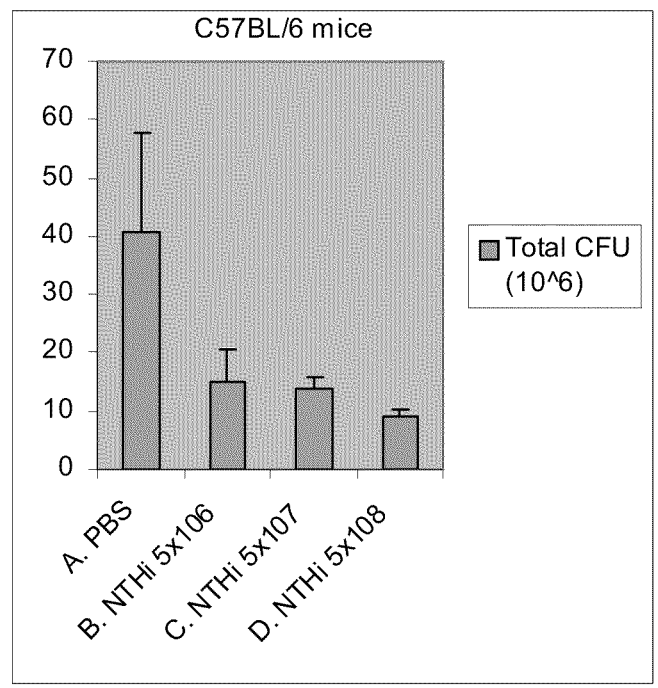
FIGS. 3A and 3B depict the mean bacteria levels in mice immunized with varying dose sizes of NTHi-164.
Figure 3B:
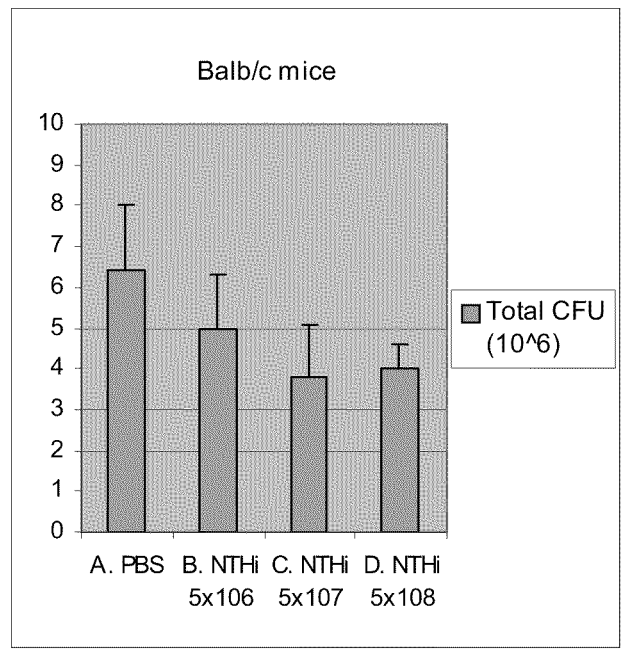

C57BL/6 or Balb/c mice were immunized by gavage with PBS or killed NTHi-164 in PBS (dose sizes $5\times10^6$, $5\times10^7$, and $5\times10^8$) on days 0 and 14. Mice were boosted intra-tracheally with a non-immunizing dose ($5\times10^5$) of killed NTHi-164 on day 20 or 21. Mice were infected intra-tracheally with $1\times10^7$ live NTHi-164 on day 27 or 28 and killed 4 h later for sampling. Levels of live Hi-164 in the lungs was measured by plating serial dilutions of broncho-alveolar lavage (BAL) fluid and lung homogenate (LH) on chocolate agar plates and culturing overnight at 37° C. in 5% $CO_2$. The colonies were counted, the number of NTHi-164 in the original BAL and LH samples calculated and the total bacteria levels in each mouse lung calculated. The mean bacteria level in each mouse group (±SEM) is shown in FIGS. 3A and 3B. Unimmunized C57BL/6 mice had higher infection levels than unimmunized Balb/c mice indicating that Balb/c mice had better innate protection. However the killed NTHi-164 vaccine was highly effective in C57BL/6 mice suggesting that the specific protective mechanism was of the Th1-type as C57BL/6 mice have been shown to have a Th1 phenotype (i.e., respond more readily with a Th1-type immune response) and the Balb/c mice more of a Th2-phenotype (i.e., respond more readily with a Th2-type response).

1.6 Capacity to Cross-Protect Against Other *H. influenzae* Isolates

This example demonstrates the broad cross-protection provided by immunization with formalin-killed NTHI-164. This would not be predicted by Sethi and Murphy (Sethy & Murphy, 2002, Clinical Microbiology Reviews 14(2):336-363) who see the lack of conservation by the major OMP P2 as being the cause of apparent lack of cross-protection in man.

Rats were immunized by the intra-tracheal route on days 0 and 14 with a vaccine comprising $5 \times 10^8$ killed NTHi-164 in 50 μL PBS. The rats were subsequently infected on day 21 with one of a variety of *H. influenzae* strains that were non-typeable strains of different biotype, or type b strains. Table 2 shows that protection was provided against all biotypes tested of the non-typeable strains. Table 3 shows that protection was also provided against 2 of 3 type b strains tested.

TABLE 2

% clearance of NTHi
% clearance of NTHi: (CFU in placebo − CFU in active) × 100/CFU in placebo

| | Infection strain (non-typeable *H. influenzae* isolates) | | | | | | | |
|---|---|---|---|---|---|---|---|---|
| Vaccine strain | Hi 289 Biotype I NTHi-166 | Isolate 1 NTHi-165 | Isolate 2 NTHi-164 | Isolate 3 NTHi-168 | Isolate 4 NTHi-167 | ATCC 43041 Biotype VII | ATCC 43095 Biotype III | ATCC 35092 Biotype VIII | ATCC 51997 Biotype V |
| Hi-164 | 87 | 82 | 87 | 91 | 83 | 74 | 85 | 78 | 89 |

TABLE 3

% clearance of *H. influenzae* type B
% clearance of NTHi: (CFU in placebo − CFU in active) × 100/CFU in placebo

| | Infection strain (*H. influenzae* type b isolate) | | |
|---|---|---|---|
| Vaccine strain | Hib 8719 | ATCC 10211 | ATCC 9795 |
| NTHi-164 | 62% | 0% | 39% |

1.7 Induction of Specific Immune Responses in Rodents

This example demonstrates that vaccination with killed NTHi-164 leads to the induction of NTHi-specific T cells, which are important in protection of the lung against bacterial infections.

Figure 4:
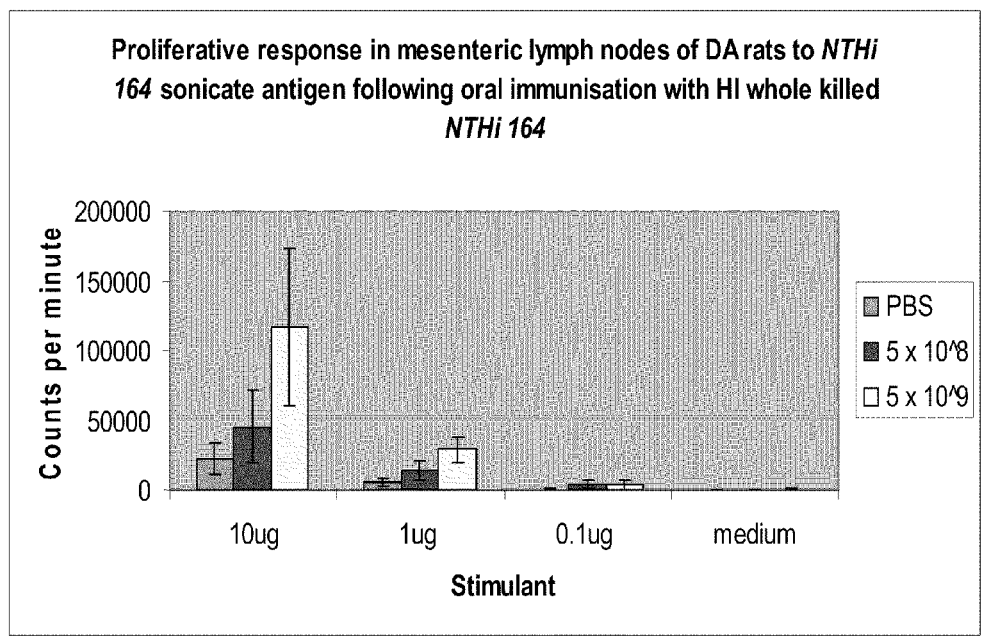
FIG. 4 depicts the mean proliferative response for mesenteric lymph node lymphocytes from rats immunized with NTHi-164.

Groups of 5 rats were immunized by instillation into the intestinal lumen (exposed by laparotomy) on day 0, of 0.5 mL of
PBS
NTHi 164 specimen at a dose of $5 \times 10^8$ in 500 μL PBS
NTHi 164 specimen at a dose of $5 \times 10^9$ in 500 μL PBS Rats were sacrificed on day 14 and mesenteric lymph nodes were collected for preparation of lymphocyte suspension and in vitro culture (in triplicate) with NTHi 164 antigen at 0.1, 1 and 10 ug/mL for 5 days. During the last 6 h of culture wells were pulsed with $^3$H-thymidine to detect lymphocytes proliferating in response to antigen stimulation, and cultures were then harvested on filter mats. Mats were placed in bags with scintillant and radioactivity (counts per minute) for each culture well, measured in a β-counter. FIG. 4 shows the mean proliferative response for lymphocytes from each rat group. This demonstrates that NTHi-164-specific lymphocytes can be detected in the mesenteric lymph nodes following immunization with killed NTHi-164.

1.8 Lack of Toxicity of Killed Isolate in Rodents

These studies provide toxicity data for HI-164OV, which suggest that the vaccine will be safe in man.

Groups of 12 Sprague-Dawley rats were dosed with PBS (placebo), a rat therapeutic dose of 2.25 mg (corresponding to $5 \times 10^9$ killed cells), or a human-size dose of 45 mg (corresponding to $1 \times 10^{11}$ killed cells) of HI-164 active substance suspended in PBS (manufacturing batch no. VRI0401). Dosing was on days 0 and 14 and rats were euthanased (pentobarbitone overdose) on day 21 for post-mortem examination and sample collection. The following parameters were measured:

Clinical assessment daily
Body weight weekly
Post-mortem examination (perform by veterinarian)
Blood biochemistry
Blood haematology
Histopathology on heart, lung, liver, spleen, kidney, stomach, pancreas, duodenum, jejunum, ileum, colon, mesenteric lymph nodes
Biochemistry, Haematology and histopathology was performed by Idexx Laboratories, Australia)

No differences were found between active treatment groups and the placebo group for any of these parameters.

1.9 Capacity to Stimulate NTHi-Specific T cells in Human Blood

This study suggests that *Haemophilus influenzae*-specific T cells in human blood recognise NTHI-164 and can secrete cytokines such as IFN-γ in response. IFN-γ is also involved in the protective mechanism whereby IFN-γ activates phagocytic cells (macrophages and polymorphonuclear cells) to more actively phagocytose and kill bacteria.

An initial study examined 4 volunteers. On day 1 blood was collected into lithium heparin tubes by venupuncture. Peripheral blood mononuclear cells (PBMC) were separated by centrifugation on a Ficoll-Paque density gradient. PBMC were cultured in serum-free medium in wells of a flat-bottom 96 well plate. Cultures were unstimulated (medium only) or stimulated with $2 \times 10^6$ and $2 \times 10^8$/mL of killed HI-164 or 10 μg/mL, 1 μg/mL and 0.1 μg/mL of NTHi 164 sonicate antigen for 3 days in an incubator set at 37° C. plus 5% $CO_2$. On day 3 culture supernatants were collected from each well into 1.5 mL eppendorf tubes, clarified by centrifugation for 2 min at 12000 rpm (g), aliquoted and stored at −70° C. until levels of IFN-γ, IL-10 and IL-12 were measured by ELISA.

Levels of IFN-γ obtained from NTHi 164 stimulated PBL culture supernatants are shown in Table 4 below:

TABLE 4

Levels of IFN-γ (pg/mL) in the culture supernatant of PBL stimulated with NTHi 164 antigen and PHA

| Antigen | MD | PH | PC | RC | Mean | SD |
|---|---|---|---|---|---|---|
| 10 ug/ml (sonicated NTHi) | 297 | 58 | 150 | 101 | 152 | 103 |
| 1 ug/ml (sonicated NTHi) | 54 | 35 | 55 | 35 | 45 | 11 |
| 0.1 ug/ml (sonicated NTHi) | <15 | <15 | <15 | 20 | 20 | |
| PHA(5 ug/ml) | <15 | 30837 | 9568 | 8617 | 16341 | 12563 |
| 2 × 10$^8$(killed NTHi) | 1738 | 1193 | 4533 | 514 | 1994 | 1764 |
| 2 × 10$^6$(killed NTHi) | 207 | 257 | 491 | 72 | 257 | 174 |
| cells only | <15 | <15 | <15 | <15 | | |
| AIM-V only | <15 | <15 | <15 | <15 | | |

A second study examined seven subjects recruited for a safety and immunogenicity study of an HI-164 vaccine. On day 0, prior to taking study medication, 10 mL of heparinized blood was received from visit 1 of Clinical Trial HHI003 subjects 001 ESY, 002 SP, 003 MBW, 004 JMW, 005 JDL, 006 RGB and 007 MA. Peripheral blood lymphocytes (PBL) were isolated on a Ficoll-Paque density gradient, washed, and resuspended in AIM-V culture medium with added amphotericin B (0.25 ug/mL), 1M Hepes Buffer and 2-mercaptoethanol (5×10$^{-5}$M)(SOP: IMM027).

Cells were cultured for 5 days in flat bottom 24 well plates at 1×10$^6$ cells/well in 1 mL of medium. Cells were stimulated with two concentrations of NTHi 164 antigen (10 μg/mL, 1 μg/mL) and PHA (5 μg/mL) (SOP: IMM011). PHA is a pan T cell stimulator.

On day 5, the culture supernatants were collected from each well, clarified by centrifugation then aliquoted and stored at −70° C. until IFN-γ levels in culture supernatant were measured by ELISA. The results are shown in Table 5 below.

TABLE 5

Levels of IFN-γ (pg/mL) in the culture supernatant of PBL stimulated with NTHi 164 antigen and PHA

| Culture stimulant | 001 ESY | 002 SP | 003 MBW | 004 JMW | 005 JDL | 006 RGB | 007 MA |
|---|---|---|---|---|---|---|---|
| 10 μg/mL NTHi 164 | 368 | 128 | 101 | 169 | 356 | 565 | 334 |
| 1 μg/mL NTHi 164 | 130 | 287 | 24 | 111 | 156 | 86 | 35 |
| 0 μg/mL NTHi 164 | 0 | 0 | 0 | 61.3 | 0 | 0 | 0 |
| 5 μg/mL PHA | 0 | 9 | 0 | 38 | 9457 | 626 | 6 |
| AIM V | 0 | 0 | 0 | 0 | 0 | 0 | 0 |

NTHi 164 (10 μg/mL and 1 μg/mL) stimulated production of IFN-γ in PBL culture supernatant of all subjects.

Capacity to Induce Specific T Lymphocyte Immune Response in Humans

Figure 5A:
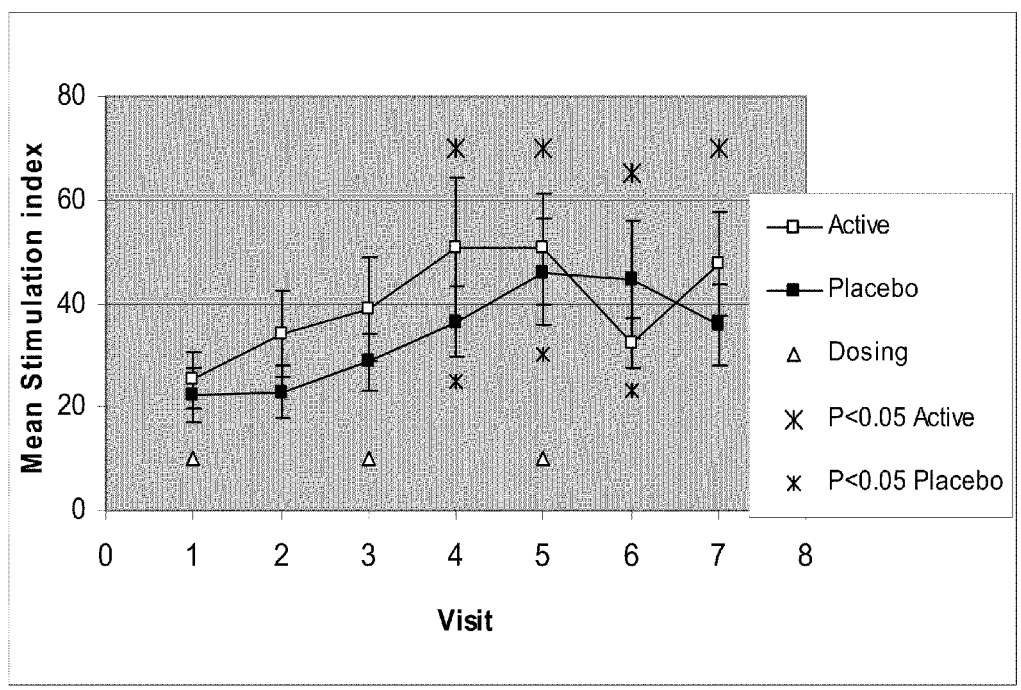
FIGS. 5A-5C depicts lymphocyte proliferation in human subjects in response to vaccination with HI-164.
Figure 5B:
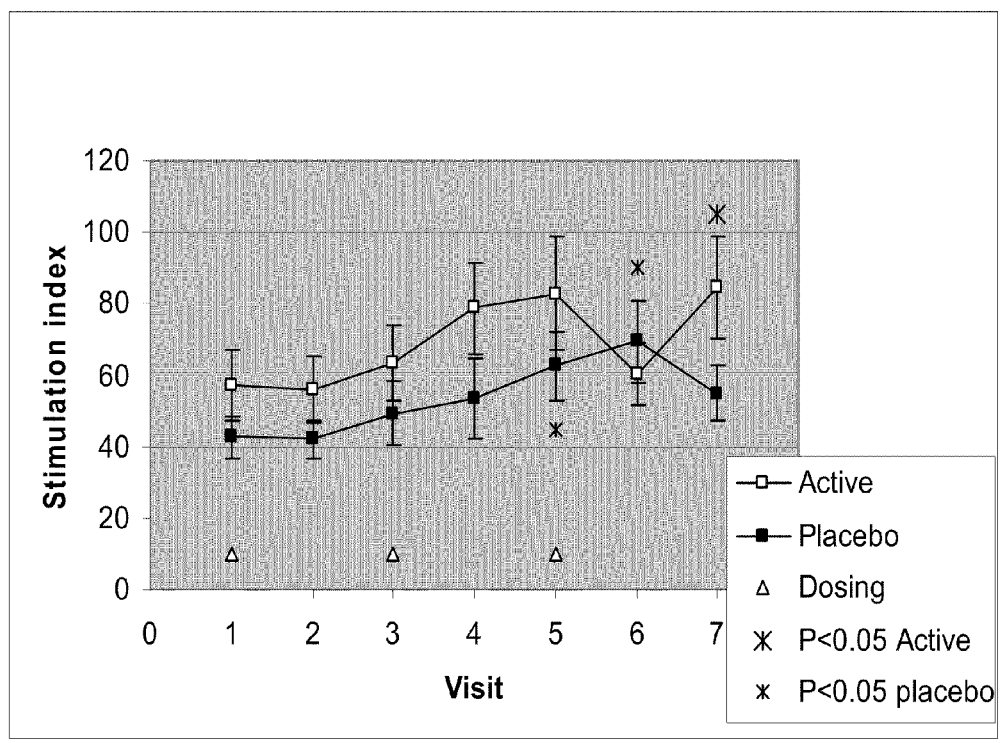
Figure 5C:
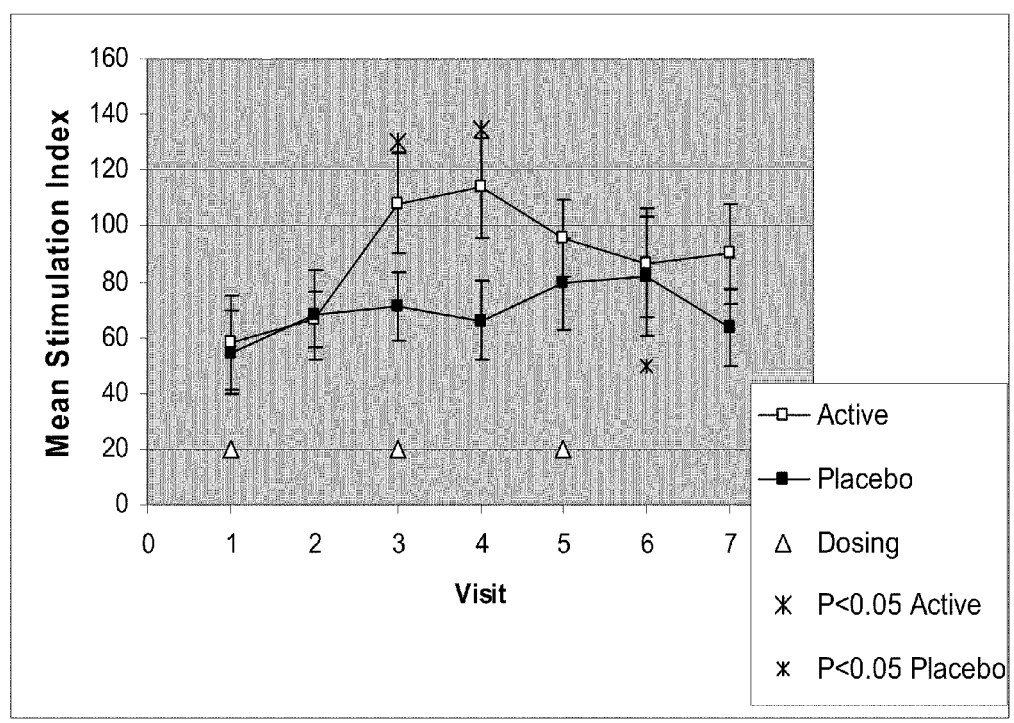

Subjects recruited to a placebo-controlled safety and immunogenicity study were examined for specific immune response induction. FIG. 4 shows the induction of specific T lymphocytes that occurred in the vaccine and placebo treatment groups over the course of the study. The specific T lymphocytes in the blood of the placebo patient group increased over the period of the study (FIGS. 5A, 5B). This response was most likely induced by exposure to *H. influenzae* bacteria during this period. In patients given the active tablet treatment the induction of specific lymphocytes was enhanced suggesting a boosting of the naturally-induced immune response. An enhanced response to PHA in vitro was also observed in blood lymphocytes from the HI-164OV group (FIG. 5C).

1.10 HI-164OV Treatment Reduces Salivary Lysozyme

Figure 6:
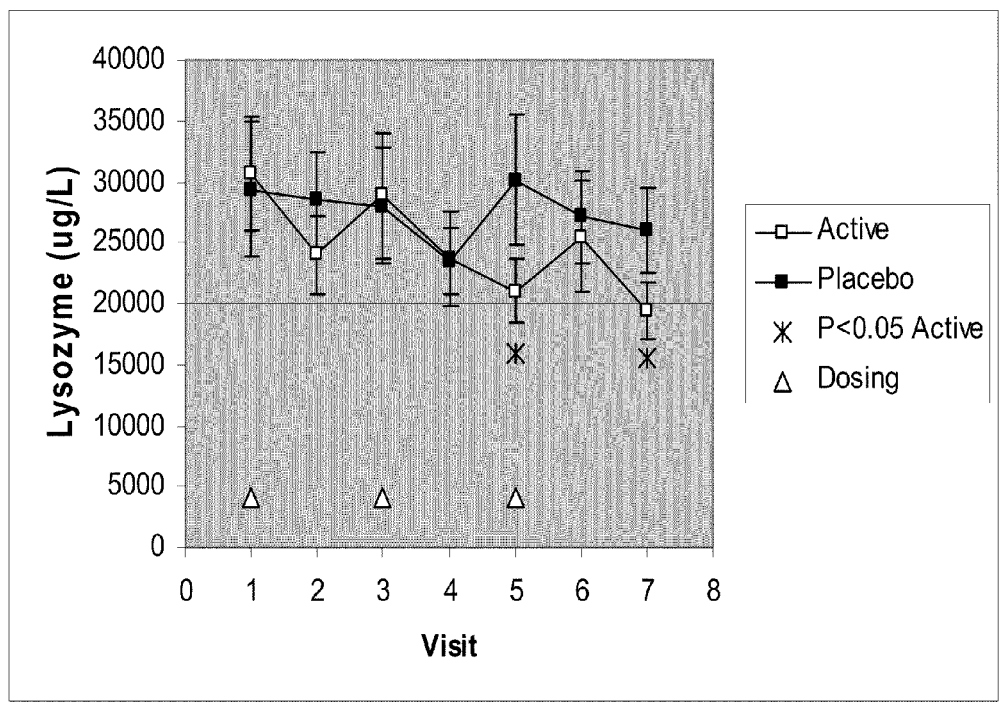
FIG. 6 depicts saliva lysozyme (mean±SEM) in human subjects following vaccination with HI-164.

The observation of reduction in salivary lysozyme in the HI-164OV treated group suggests a reduction in inflammation. (FIG. 6)

1.11 Capacity of a Killed NTHi-164 Oral Vaccine (HI-164OV) to Prevent Bacteria Reaching the Lower Airways The same subjects as described above were examined for relationship between serum IgG and number of visits at which NTHi was detected in throat gargles. The mean (±SEM) log change in serum NTHi-specific IgG between visits 1 and 6 was plotted against the number of visits (classified as either 0-1 visits or 2-4 visits) at which *H. influenzae* was detected in the gargle (FIG. 7A). In the placebo group high levels of serum NTHi-specific IgG were associated with live NTHi detection at 2 or more visits. No such association was apparent with subjects treated with the active HI-164OV tablets. A plot of median change in serum IgG from base is shown in FIG. 7B for all visits 2-7. Again this demonstrates an increase in serum NTHI-specific IgG in the placebo treatment group and a reduction in serum NTHi-specific IgG in the HI-164OV treatment group. This data was interpreted as the active treatment preventing bacteria in the upper airways from entering the lower airways and inducing *H. influenzae*-specific IgG in the serum. Median change from baseline (visit 1) in serum NTHi-specific IgG for subjects with 0-1 or 2-6 visits at which *H. influenzae* was detected in the gargle is shown in FIG. 7B.

1.12 Capacity of a Killed NTHi-164 Oral Vaccine (HI-164OV) to provide protection Against Severity of Exacerbations in Patients with Mild-to-Moderate or Moderate-to-Severe Airway Disease.

In a double-blind, placebo-controlled parallel clinical study examining the efficacy of the HI-164OV vaccine 164 patients with mild-to-moderate or moderate-to-severe airway disease were dosed with 18 tablets containing 45 mg (equivalent to 10$^{11}$ killed bacteria). Two tablets per day were given on days 1, 2, 3, 29, 30, 31, 57, 58, 59. General health, adverse events, acute exacerbations of chronic bronchitis and severity of these exacerbations was monitored. It was found that the active treatment group had a considerable reduction in hospitalisations (largely due to exacerbations of bronchitis) compared to the placebo control group (7 patients with 10 hopitalisations in the placebo group and 1 patient with 1 hospitalisation in the HI-164OV group). These data are indicative of the protective capacity of this vaccine active substance when used as an oral vaccine.

Example 2: Clinical Benefits of HI-164oV

A placebo-controlled double-blind clinical study was performed in which 64 subjects on the basis of having smoked at least 10 cigarettes per day for the past two years were recruited and allocated to oral NTHi therapy or placebo treatment groups in a double-blind study. Subjects were randomized into placebo and active groups and were given three courses of study medication at monthly intervals. Each course consisted of two tablets per day for three days. The active tablets each contained 45 mg of formalin-killed NTHi (equivalent to $10^{11}$ killed bacteria per active tablet). Blood, saliva, gargles, throat swabs, and nasal swabs (for microbiological assessment) were collected at seven fortnightly visits.

1.13 Detection of NTHi and Measurement of NTHi-Specific IgG

Figure 8:
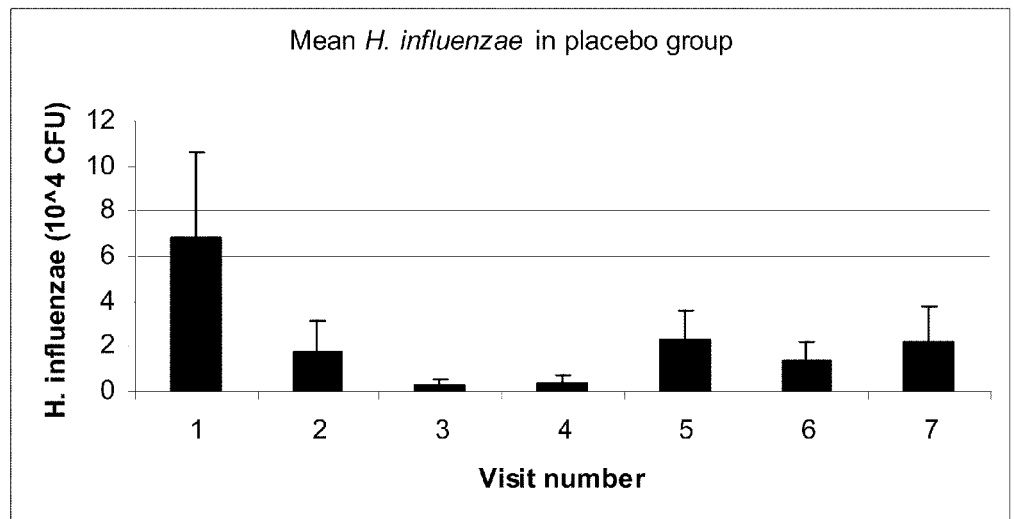
FIG. 8 is a graph showing mean number of NTHi isolated in gargle of a placebo-dosed human subject study group.

Surprisingly, measurements in the placebo-treated and vaccine-treated groups over the winter period detected NTHi in both groups indicating random exposure to the bacterium. FIG. 8 shows the mean level of NTHi in the gargles of the placebo group at each visit.

NTHi-specific IgG was measured in serum and saliva by ELISA assay. Briefly, wells of 96-well Nunc Maxisorp plates were coated with *H. influenzae* 164 sonicate antigen preparation. After incubation overnight at 2-8° C. the plates were washed and samples of serum or saliva at various dilutions were added. Following incubation at room temperature for 60 minutes, the plates were washed and horseradish peroxidise-conjugated anti-human IgG antibody (Chemicon catalogue number AP112P) was added. After incubation for a further 60 minutes at room temperature the plates were washed and TMB substrate (Biomediq catalogue number 50-76.00) was added prior to an additional incubation for 10 minutes at room temperature and the reaction being stopped by addition of 1M phosphoric acid. Absorbance was read on a BioRad microplate reader on dual wavelength mode with a primary filter of 450 nm and reference filter of 655 nm. A standard curve was used to determine the ELISA units in each sample.

Figure 7:
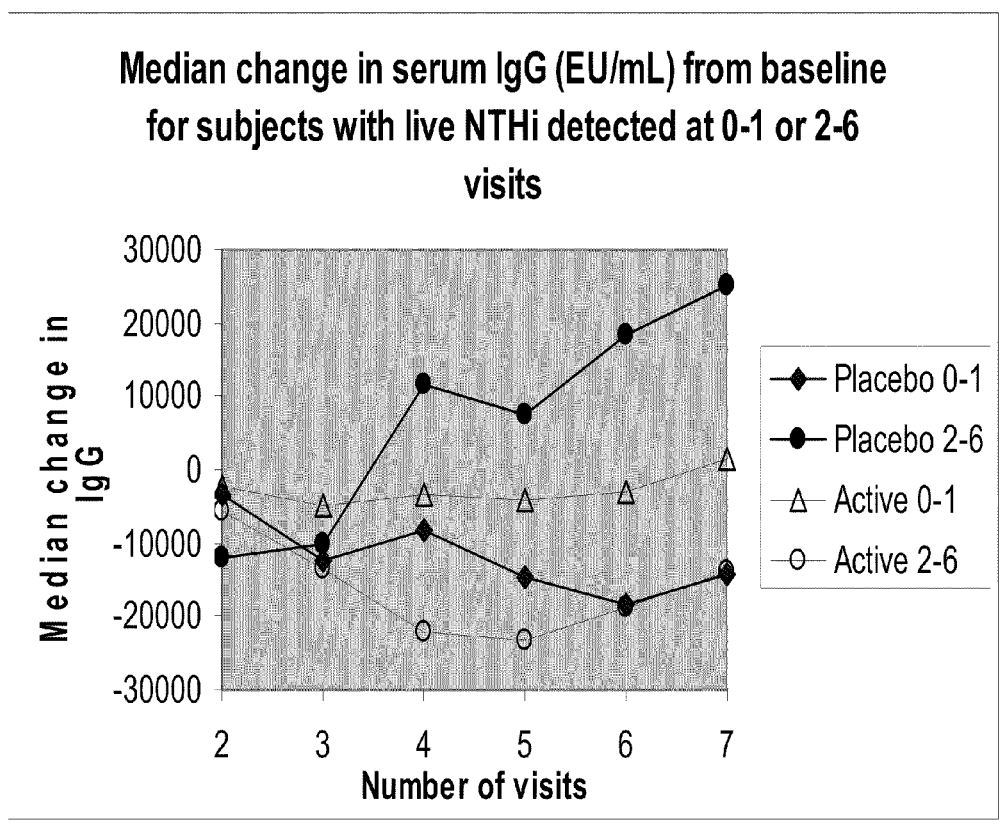
FIG. 7 shows the effect of vaccination of human subjects with HI-164 on serum IgG levels.
Figure 9:
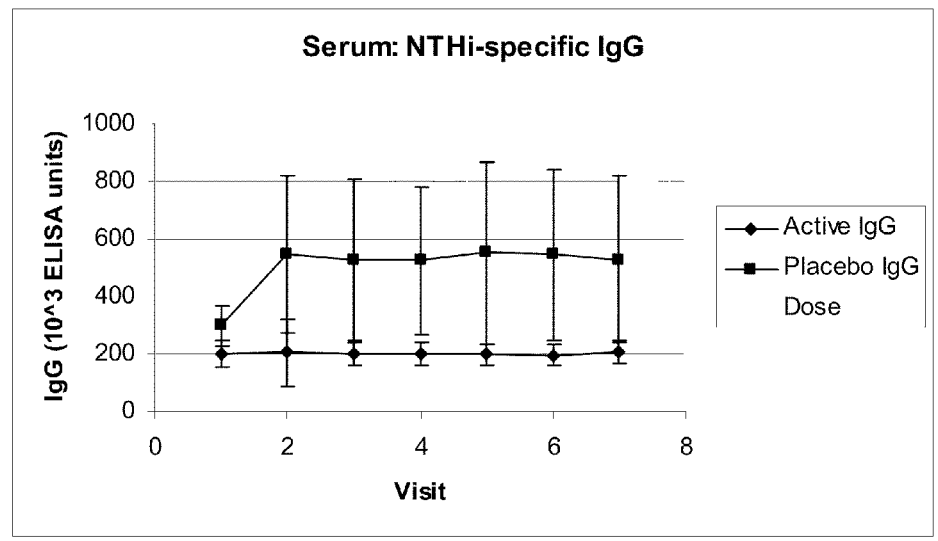
FIG. 9 is a graph showing serum NTHi-specific IgG levels in human subjects in the placebo group and a treatment group immunized with an oral killed NTHi vaccine.
Figure 10:
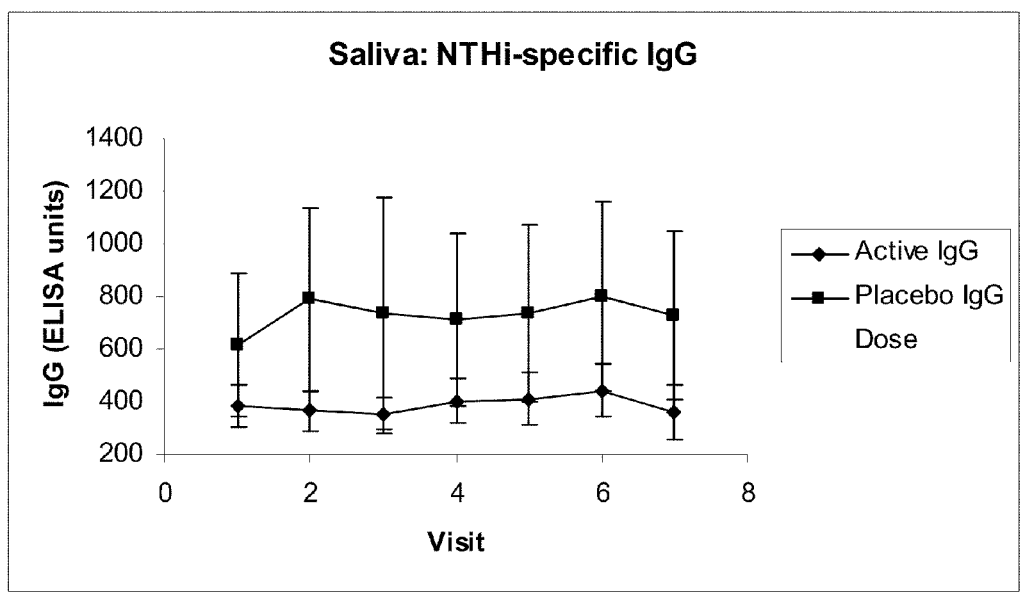
FIG. 10 is a graph showing saliva NTHi-specific IgG levels in human subjects in the placebo group and the treatment group immunized with an oral killed NTHi vaccine.

Levels of NTHi-specific IgG in serum and saliva in the placebo group were higher and more variable than the levels in the vaccine-treated group (see FIG. 9 and FIG. 10). Applicants believe this because NTHi reaching the lower airways in the placebo group results in systemic production of IgG and that was essentially prevented from reaching the lower airways in the vaccine treated group. To test this, plots were prepared of relationship between the number of visits at which NTHi was detected in the gargle and the median change in serum IgG between visits 1 and 6 (FIG. 7). Placebo and active subjects were grouped according to whether they had 0-1 visits or 2-6 visits where NTHi was found in the gargle. In the placebo group, positive increases in serum IgG were associated with increased number of NTHi detections. This was not found in the active treatment group. The difference between the placebo and active change in IgG was statistically significant (p=0.0186) indicating the serum IgG in the placebo group was indeed generated by NTHi as a result of the bacteria reaching the lower airways. Moreover, the more NTHi present in the placebo washings, the higher the IgG antibody level. This is also believed to apply to the appearance of salivary NTHi specific IgG in the placebo group.

1.14 Discussion

Serum IgG antibody as a marker for the efficacy of the vaccine was measured. An apparent lack of an IgG response in the vaccine-treated group was found while the placebo treated group of patients showed an increase in serum IgG. Without being limited by theory, it is believed by the applicants that the increase in IgG observed in the placebo group is reflecting an immune response to infecting bacteria reaching the lower airways where uptake of the bacteria by antigen-presenting cells and transport to draining lymph nodes induces an anti-bacterial IgG response. In contrast, the lack of such a response in the vaccine-treated group indicates that the bacteria are being essentially prevented (by a mucosal vaccine-specific immune response) from reaching the lower airways. A comparison of the IgG response in subjects with NTHi detected in the upper airways at low frequency (detected at 0-1 visits) or at high frequency (detected at 2-6 visits) also showed the increase in IgG in the placebo group but not in the active (vaccine) treatment group. This suggests that serum IgG measurement following oral vaccination with NTHi reflects exposure to infection and the degree to which this is prevented by mucosal immunization. The saliva IgG response reflected that seen in the serum.

Overall, this study demonstrates detection of NTHi in the upper respiratory tract of subjects in both the treatment and placebo groups, and that treatment with oral killed NTHi vaccine therapy led to a reduction NTHi-specific IgG in serum and saliva in the treatment group indicating the vaccine was successful in limiting or preventing access of NTHi to the lower airways (i.e., less allergen to initiate asthma or aggravate COPD).

Thus, only in the placebo group did NTHi access the lower airways as evidenced by stimulation of IgG antibody, and oral 'immunization' with NTHi vaccine reduced NTHi allergen in the airways.

Example 3: Killed Nthi-164 Vaccine (HI-164OV) Orally Administered to Subjects with Mild, Moderate or Severe Airway Disease Reduced Usages of Anti-Asthma Therapy One hundred and forty human subjects with mild-to-moderate or moderate-to-severe airway disease were recruited into a double blind, placebo-controlled study to assess the effect of an oral killed non-typeable *Haemophilus influenzae* (NTHi) vaccine on number and severity of wheezy reversible airways obstruction, and usage of concomitant medication as well as the presence of NTHi and other bacteria in the airways.

A reduction in use of anti-asthma-type medication (bronchodilators, steroids etc) and reduced infection by NTHi was found in the treatment group compared to the control group. In particular, a specific reduction of NTHi within the airways of subjects with high IgE antibody levels (serum and secretions) to NTHi, and a reduction in asthma symptoms with a consequential reduction in the need for asthma medication was obtained.

1.15 Subjects and Clinical Trial

This study was a multi-center, double blind, placebo controlled trial conducted at four sites under the supervision of a Clinical Research Organisation. These sites were: Hollywood Private Hospital, Perth, Wash. (Dr M. K. Tandon); Sir Charles Gairdner Hospital, Perth, Wash. (Dr M. Phillips); Royal Perth Hospital, Perth, Wash. (Assoc. Prof. G. Waterer) and the University of Newcastle, Newcastle, NSW (Prof R. Clancy). Identical protocols were accepted by the ethics committees of each institution, and the studies conformed to the guidelines of these committees. The main admission criterion was a history of two or more episodes per year, for two consecutive years (an 'episode' was defined as 'an increase in cough and purulent sputum from background levels'). Subjects were stratified into two groups: i) patients with an $FEV_1$ of ≤50% of predicted normal value (38 subjects), and ii) patients with $FEV_1$ of >50% of predicted normal value (102 subjects). This second group included patients with COPD, patients with a primary diagnosis of bronchiectasis and patients with 'normal' $FEV_1$ levels. Patients from the two study groups with a FEV<80% and without a primary diagnosis of bronchiectasis, were defined as having COPD and are the subject of this analysis. The analysis examines the treatment with HI-164OV in all COPD patients and then specifically treatment in the moderate to severe COPD patient group.

All subjects were followed for 8-9 months, over the southern winter and early spring: Recruitment began 7 Mar. 2006 and the last patient completed 31 Oct. 2006. HI-164OV tablets contained 45 mg (equivalent of CFU $10^{11}$ bacteria) of formalin-inactivated HI-164, provided as enteric coated tablets; placebo tablets containing excipients only, were provided as enteric-coated tablets for oral administration. Patients took 3 courses of tablets. Each course consisted of 2 tablets daily for 3 consecutive days (before breakfast), with courses repeated at day 28 and day 56. Subjects had face-face interviews at weeks 0, 4, 8, 12, 18, 24, 30, 36. At weeks 4 and 8 the next tablet course was given. At all visits acute episodes and their characteristics were documented with the aid of a structured questionnaire; adverse events were logged; sputum and blood was collected to monitor bacterial colonization and safety parameters respectively; and concomitant medications assessed.

The primary variables assessed for this analysis were (i) the number of exacerbations (defined as 'an increase in volume and purulence of sputum'); (ii) the proportion of subjects experiencing one or more exacerbations; (iii) the mean duration of exacerbations; (iv) the number of antibiotic courses prescribed for exacerbations. The secondary variables assessed were adverse effects (including hospitalisation), and bacteriology of sputum.

Statistical analysis on the intention-to-treat population used 'P values' considered as two-sided. Rates of acute episodes (or 'acute episodes defined by treatment') were calculated as number of events divided by exposure (calculated as number of days from randomization until last visit) multiplied by 100. Repeated measures Poisson regression was used to examine treatment differences in rates, where the logarithm of exposure (in days) was considered an offset. Rate (risk) ratios and their associated 95% confidence intervals (CI) were obtained from these regressions. Fisher's exact test was used to compare the proportions of subjects with one or more episodes. Durations of episodes (start date to stop date) were estimated via the Kaplan-Meier procedure and treatment differences were analyzed by the log-rank test. For calculation of treatment days, the number of days was calculated as the sum of duration of each pertinent medication regardless of overlap in terms of start and stop dates. The number of days each subject received treatment was compared between treatments using Wilcoxon's rank-sum test (student's 't' approximation). The number of subjects experiencing 0, 1, 2 etc. antibiotic courses was presented and treatment groups were compared using the Cocharan-Mantel-Haenszel test. Hospitalization rates were compared between treatments using Poisson regression, where the log-transformed number of subjects was used as an offset.

The aim was to recruit 124 in each of the moderate-severe and the mild-moderate groups, allowing for a 20% drop out rate. With 50 in each group completing the study this would (at the 5% significance level and with 80% power) detect a relative risk reduction in number of episodes of 37% (assuming an infection rate in the placebo group of 2); a reduction in the proportion of patients at 28% (assuming 80% of the placebo group have at least one infection); a relative risk reduction of prescribing antibiotics of 33% (assuming a prescription rate of 2.4 in the placebo group); a difference in mean days of duration of 1.2 assuming a SD of 2 days in the placebo group. The requirement of 2 or more episodes per year for 2 years proved a major impediment to recruitment, with a total of 73 being enrolled with COPD (38 with moderate-severe disease and 35 with mild-moderate disease). An additional 67 subjects with bronchiectasis or with 'normal' $FEV_1$ values as a percentage of predicted normal (i.e., ≥80%) were studied, but are not included in this analysis of those with COPD. Pooled analysis was a pre-study decision.

1.15.1 Demographic Characteristics

The patient characteristics are set forth in Table 6 below.

TABLE 6

Patient characteristics

| | All Subjects with COPD | | Subjects with moderate-severe COPD | |
|---|---|---|---|---|
| Characteristic | Placebo (37) | HI-164OV (36) | Placebo (20) | HI-164OV (18) |
| Age (years) (median, range) | 68.8 (41-88) | 62.8 (47-87) | 67.8 (55-88) | 69.5 (47-87) |
| Sex (male/female) | 25:12 | 25:11 | 14:6 | 15:3 |
| Ever-smoked | 30 | 31 | 15 | 15 |
| Current smoker (median, range) | 6 | 7 | 4 | 2 |
| $FEV_1$ (l/sec) (median, range) | 1.17 (0.4-3.0) | 1.32 (0.5-2.6) | 0.89 (0.4-2.0) | 1.0 (0.5-1.5) |

At baseline in those with moderate-severe COPD, in the active group and 13 in the placebo group had a history of ischaemic heart disease, 6 in the active group and 2 in the placebo group had a past history of 'asthma', 2 in the active group and 4 in the placebo group had an associated bronchiectasis. In this group relevant therapy at baseline was: 12 subjects in each group took salbutamol; 14 in the active group and 13 in the placebo group took tiotropium; and 10 in the active group and 9 in the placebo group received salmeterol/fluticosone (Seretide®). Prednisone was taken by 6 in the active group and 7 in the placebo group. Oxygen therapy was used by 5 in the active group and 2 in the placebo group. Approximately half of both placebo and active groups had pre-seasonal influenza vaccination, while two thirds had had pneumococcal vaccination.

1.16 Results

The results of HI-164OV administration vs. placebo are set forth in Table 7 below:

1.16.3 Duration of Episodes

The mean duration of episodes was less in active compared to placebo groups ('all COPD': 14.7 compared to 17.3

TABLE 7

Summary of results

| | Total COPD Population | | | Moderate-Severe COPD | | |
|---|---|---|---|---|---|---|
| | HI-164OV (36) | Placebo (37) | Protection (%) (P value) | HI-164OV (18) | Placebo (20) | Protection (%) (P value) |
| Number of acute episodes (subject number) | | | | | | |
| Total | 36 (24) | 50 (25) | 24 (0.19) | 22 (13) | 29 (13) | 17 (0.52) |
| Antibiotic-treated | 28 (20) | 38 (23) | 24 (0.26) | 15 (11) | 23 (13) | 27 (0.33) |
| Corticosteroid-treated | 9 (10) | 21 (15) | 50 (0.06) | 5 (4) | 15 (10) | 62 (0.05) |
| Antibiotic Treatment | | | | | | |
| courses | 37 (20) | 70 (23) | 46 (0.03) | 19 (11) | 48 (13) | 56 (0.03) |
| total days (subject number) | 284 (20) | 735 (23) | 72 (0.01) | 136 (11) | 543 (13) | 60 (0.01) |
| Oral and Acute Corticosteroid Treatment | | | | | | |
| days (subject number) | 127 (9) | 344 (16) | 56 (0.26) | 61 (4) | 289 (11) | 75 (0.26) |
| Duration of episodes | | | | | | |
| mean days (range) | 14.7 (3-81) | 17.3 (3-74) | 24 (0.19) | 14.3 (3-84) | 22.7 (4-74) | 37 (0.01) |

1.16.1 Number of Acute Episodes

Using the protocol definition of an acute episode as "an increase in volume and purulence of sputum", for the total COPD group there were 36 episodes in the HI-164OV group and 50 episodes in the placebo group, which when analyzed by monthly periods had a risk ratio of 0.76 (95% CI 0.50, 1.15; P=0.19). When analyzed over three monthly periods, at a rate of events/100 days, there was a greater benefit in the active group in the second 3 month period (Placebo: events/100 days-0.82 (first 3 months), 0.74 (second 3 months); Active: 0.72 and 0.48. P value. Period effect 0.68, and treatment effect 0.19). Using the protocol definition of acute episode ("increase in volume and purulence of sputum") in the moderate-severe COPD group there were 22 episodes in the active group compared to 29 episodes in the placebo group, with a risk ratio of 0.84 (95% CI: 0.48, 1.49), which was not significant. However, analysis by three monthly periods, the event rate/100 days was the same for active and placebo groups at 0.82 for the first 3 months, but reduced in the active group compared to placebo in the second 3 months (0.6 versus 0.85), representing a 29% reduction in incidence. In those with moderate-severe disease there was almost twice as many patients (11 subjects) in the placebo group with 2-4 episodes when compared to the active treatment group (6 subjects), consistent with an effect of therapy on reduction of recurrence. There was no or little difference in protection in the total COPD group, but a higher level of protection (27%) was noted in those with more severe disease.

1.16.2 Proportion of Patients with Acute Episodes

The proportion of patients with acute episodes was reduced by a small amount with therapy, except when only the more severe episodes were captured using the definition of 'corticosteroid-treated' episodes.

days; moderate-severe COPD 14.3 compared to 22.7 days), but this difference reached statistical significance only in the moderate-severe group (P=0.01).

1.16.4 Medication Usage

A significant reduction in both the number of prescribed courses of antibiotics and the number of days of antibiotic treatment (for exacerbations) followed active treatment in both the total group of subjects with COPD and those with moderate-severe COPD. Protection was statistically significant in both 'all COPD' and moderate-severe COPD patient groups, for both forms of analysis. Fewer patients received three or more courses of antibiotics in the active group than in the placebo group (for 'all COPD', 5 versus 14 patients' for moderate-severe COPD, 2 versus 11 patients), supporting protection against recurrent episodes.

Subjects that had moderate to severe COPD and were treated with the oral vaccine, were found to have a 50% reduction in the usage of bronchodilator therapies in the active group. Eosinophil counts following the administration of triple course of oral NTHi therapy were found to have significantly reduced in only the active group. In conclusion, the oral NTHi therapy reduces the usage of bronchodilator therapies in acute episodes and also reduces eosinophil counts which are connected allergic reactions specific to NTHi.

1.16.5 Admission to a Hospital

The rate of hospital admission for exacerbation of COPD was high (see Table 8 below), with 10 admissions in 7 patients in the placebo group (20 subjects) in moderate-severe COPD. For those with less severe COPD (17 subjects) only two were admitted to hospital for an exacerbation of COPD through the period of the study. Protection against admission to hospital due to an exacerbation of COPD in 'all COPD' was 61% and of borderline significance (P=0.07) while in those with moderate-severe COPD, a higher level of protection was found (90%) which was significant (P=0.01). In this more severe group, a significant difference in 'hospitalisation for all causes' was detected (P=0.04), but numbers were too small to identify an independent effect on hospital admission for non-respiratory events.

1.16.6 Sputum Bacteriology

Analysis of 'acute event' sputum samples gave information of little value due to antibiotic treatment, transport delays and late notifications. Specimens collected at regular visits following the onset of the study were considered valid if cultures were made less than 4 hours from collection, and saliva contaminated specimens (detected by presence of epithelial cells) were excluded. For these 'routine' samples in the placebo group for 'all COPD' (37 subjects), half the patients (19 subjects) had positive cultures with a total of 88 positive cultures. The equivalent figures for the active group (36 subjects) were 13 subjects with 45 positive cultures, i.e., following HI-164OV therapy there were less subjects (by 31%) having positive sputum cultures for respiratory pathogens, with the total number of positive sputum cultures being approximately half that in the placebo group. In the placebo group NTHi was isolated in 14 subjects on an average of 2.8 occasions. For other pathogens: *M. catarrhalis* was isolated in 5 subjects (average 2.4 occasions); *S. pneumoniae* in 6 subjects (average 1.7 occasions); *P. aeruginosa* in 11 subjects (average 2.3 occasions). In the active group NTHi was isolated in 8 subjects (average 2.9 occasions); *M. catarrhalis* in 7 subjects (average 1.0 occasion); *S. pneumoniae* in 4 subjects (average 1.5 occasions); *P. aeruginosa* in 3 subjects (average 3 occasions). Further analysis showed in the placebo group the 21 subjects with positive sputum cultures had 34 acute episodes (1.62 per subject) while the 16 without positive samples had 16 acute episodes (1.0 per subject). For the active group, 14 with positive cultures had 20 acute episodes (1.42 per subject) and 22 with a positive sputum culture had 16 acute episodes (0.73 per subject). For NTHi isolates, a similar pattern was shown (placebo: positive culture in 14 subjects with 20 acute episodes (1.42 per subject) and no growth in 23 who had 30 acute episodes (1.31 per subject); active: 8 subjects with positive cultures had 10 episodes (1.25 per subject) while 28 with no growth had 26 episodes (0.93 per subject). It is concluded (i) that a positive sputum culture predicts a greater risk of having an acute clinical episode (irrespective of whether the subject is in the placebo or active group), (ii) that in the active group, there is apparent protection in both culture positive and culture negative groups (approximately 12% in the culture positive group—calculated as infection episode/person value of 1.42 in the active versus 1.62 in placebo group; and approximately 27% in the 'non culture positive' group—calculated as infection episode/person value of 0.73 in the active versus 1.0 in placebo group), (iii) HI-164OV oral therapy is followed by less of positive cultures. These 'no growth' cultures are associated with less exacerbations (above). A similar analysis of NTHi positive sputa gave almost identical outcomes with respect to the protective effect of oral HI-164OV therapy (data not shown).

TABLE 8

| | Hospitalization | | | | | |
|---|---|---|---|---|---|---|
| | HI-164OV | | Placebo | | P value | |
| | Number of events | Number of patients | Number of events | Number of patients | 1 | 2 |
| (a) All COPD | | | | | | |
| All Hospitalization events | 8 | 8 | 16 | 12 | 0.12 | 0.50 |
| Hospitalization for exacerbations of COPD | 5 | 5 | 13 | 9 | 0.07 | 0.48 |
| (b) Moderate-severe COPD | | | | | | |
| All Hospitalization events | 3 | 3 | 12 | 8 | 0.04 | 0.53 |
| Hospitalization for exacerbation of COPD | 1 | 1 | 10 | 7 | 0.01 | 0.87 |

P(1) compares hospitalization rates in all subjects.
P(2) compares hospitalization rates in hospitalized subjects.

TABLE 9

Protection in active versus placebo in sputum negative subjects

| | | No. subjects with sputum samples (no. acute episodes) | No. subjects with sputum samples (no. acute episodes) | Active | Placebo | |
|---|---|---|---|---|---|---|
| Any pathogen grown in routine sputum samples | + | 21 (34) | 14 (20) | 1.42 | 1.62 | 12 |
| | − | 16 (16) | 22 (16) | 0.73 | 1.0 | 27 |
| Non-typeable *Haemophilus influenzae* grown in routine sputum samples | + | 14 (20) | 8 (10) | 1.25 | 1.42 | 12 |
| | − | 23 (30) | 28 (26) | 0.93 | 1.31 | 29 |

TABLE 10

Protection in active versus placebo in sputum negative subjects

| | Percentage of Subjects (%) | | Percentage of Clinical Protection (%) | |
|---|---|---|---|---|
| Organisms isolated from sputum | HI-164OV | Placebo | culture + ve | culture − ve |
| Any pathogen grown in routine sputum samples | 36 | 51 | 12 | 27 |

TABLE 10-continued

Protection in active versus placebo in sputum negative subjects

| Organisms isolated from sputum | Percentage of Subjects (%) | | Percentage of Clinical Protection (%) | |
|---|---|---|---|---|
| | HI-164OV | Placebo | culture + ve | culture − ve |
| Non-typeable *Haemophilus influenzae* grown in routine sputum samples | 22 | 38 | 12 | 29 |

Tables 9 and 10 demonstrate the percentage of bacteria grown from various sputum samples of the subjects/patients. The Active Group was treated with HI164OV product.

1.17 Discussion

Acute exacerbations as key events in the natural history of COPD are recognized as particular targets for intervention therapy in current guidelines. To determine the impact of immunotherapy with an oral vaccine (HI-164OV) prepared from a novel isolate of NTHi (NTHI-164) on the incidence and severity of exacerbations, subjects with COPD who had a history of recurrent exacerbations were studies. Such subjects however, represent only 20-25% of all those with COPD, which led in the present study to an enrolment less than was planned. This difficulty was further complicated by the use of a classical descriptive definition of acute episodes as 'an increase in volume and purulence of sputum'. While this definition reflects the infective origin of acute episodes, it can be imprecise given the variable background level of intrabronchial inflammation in COPD, blurring distinction of discrete episodes. Despite limitations imposed by definitions, two conclusions can be taken from this study. First, subjects with COPD and recurrent exacerbations benefit from oral immunotherapy with HI-164OV, in particular with a reduction in their severity. Second, those with moderate-severe COPD benefit to a greater extent than do those with milder disease.

Although there was a trend to a reduction in incidence of exacerbations in 'all COPD' using the descriptive definition of increase in sputum purulence, several observations support this outcome measure as having clinical relevance. Analysis in the placebo group showed a high event rate at the beginning of the study. A higher protection level at 35% in the second three months of this study is therefore consistent with a delayed onset of immune enhancement, with results in the second half of the study a more accurate reflection of protection. Moreover, the placebo group included more than twice the number of subjects having 2-4 episodes, suggesting that HI-164OV treatment is particularly effective in preventing recurrent episodes. Persuasive data come from the analysis of episodes defined in terms of treatment, especially with corticosteroids, when there was a protection level in excess of 50%. These data sets showing clearer cut protection for more severe episodes, indicate that the main value of immunotherapy relates to reduction in parameters of exacerbation severity, at least in those with COPD and frequent episodes.

There was a difference in parameters of severity following active treatment with a consistency of benefit in all parameters of severity, with HI-164OV treatment followed by shorter episodes, less treatment with antibiotics and oral corticosteroids, and less chance of hospitalization. Usage of antibiotics in terms of courses prescribed, or days taken, was an improved index of benefit rather than simply analyzing number of episodes treated with antibiotics, suggesting that most episodes of purulent sputum will be treated with an antibiotic irrespective of severity, but only those considered to be clinically severe will attract repeat courses. The significant reduction in hospitalization in those with moderate-severe disease is an impressive outcome given the small sample size. Applicants are unaware of any other intervention therapy having a similar ability to reduce hospitalization rate. The numbers are small, and this outcome was only significant in the group with moderate-severe COPD, but this is consistent with improvement in all other parameters of severity having the greatest impact in those with moderate-severe disease. This may reflect a greater clinical benefit for any given reduction in airways inflammation, in those with the most compromised airways.

The standard for comparison of therapy aimed at reducing the impact of acute exacerbations in COPD is fluticasone/salmeterol (500/50 mcg). Studies of this combination included large numbers of subjects with primary outcomes measuring retention of flow rates or all-cause mortality. Subjects included in the studies had moderate-severe COPD, but were not selected because of frequent acute episodes as in the present study. A protection level of about 40% against acute episodes defined by corticosteroid-therapy was observed in each study, less than in the HI-164OV study but with significance levels reflecting the greater power possible with large numbers. Benefit was particularly noted in those with more severe disease, as found in the HI-164OV study. However, fluticasone/salmeterol protected little if at all (0% and 17%) against 'severe' exacerbations defined as requiring admission to hospital, in contrast to the data obtained using HI-164OV. It is noted that in this study that the hospitalization rate of about 9% per annum, compared to a higher rate in the present study by two to three fold. This higher rate probably reflects frequent exacerbations as a marker of more severe disease. When acute episodes were defined in terms of antibiotic-therapy, however, there was an increase in number of episodes in the active group. This contrasted with a reduction of antibiotic-treated episodes in the HI-164OV study. The increase in antibiotic-defined acute episodes is consistent with an inhaled steroid-related proneness to infection (oropharyngeal thrush and pneumonia).

Early longitudinal studies of patients with COPD failed to clarify the role played by bacteria in pathogenesis mainly because the rate of isolation of bacteria in sputum during stable disease was similar to that during acute episodes. Recent prospective studies have used molecular typing to demonstrate an association between new strains of bacterial pathogens with exacerbations of COPD. Isolation frequencies of bacteria in this latter study, in routine sputum samples, were very similar to those found in the present study, and the isolation of a pathogen was significantly associated with a current exacerbation. The trend in the data from the present studies obtained in stable disease, is consistent with these concepts: positive sputum culture appeared to be a risk factor for acute exacerbations (irrespective of whether the subject was in the placebo or active limb of the study); and comparing active with placebo, added protection is noted in the active group in both those growing pathogens and those who do not. These outcomes could reflect enhanced mucosal resistance to acquisition of 'novel' bacterial strains, and/or to a reduction in the level of bacteria colonization of the airways, that resists pro-inflammatory events such an intercurrent virus infection. In either situation a specific activation of Peyer's patch-derived T cells by NTHi antigens mediates a recruitment and activation of phagocytic cells which serve as a non specific effector mechanism.

Oral immunotherapy with killed NTHi (HI-164OV vaccine) activates the Gut-Associated Lymphoid Tissue (GALT), with specific T lymphocytes homing to the bronchus mucosa. Recent studies have shown that aspiration of bronchus contents into the gut is a physiological mechanism of antigen presentation to the GALT, and that oral administration of HI-164OV serves to optimize a seasonal process of T cell activation. HI-164OV is a different product to the polybacterial extracts used widely in Europe for 'immune protection'. It contains a single species of bacteria, formulated as a whole cell preparation at a concentration several logs greater than those used in the polybacterial products, so as to drive a specific Peyer's patch immune response. Analysis of studies using polybacterial isolates in subjects with chronic airways disease failed to show significant reduction in exacerbations, an outcome also found in a comparative study between a polybacterial product and oral NTHi immunotherapy.

Example 4: NTHI-164 Conveys a Greater Degree of Cross-Protection than NTHI-166 in Challenge Experiments NTHI-164 and NTHI-166 (NTHi289) tested as vaccines in a rat model of intra-tracheal (IT) immunization and acute respiratory infection challenge with a panel of NTHi isolates gave different levels of protection. The isolates used in the infection challenge were NTHI-164, NTHi-165, NTHI-166, NTHI-167, NTHi-168, ATCC 3041, ATCC 43095, ATCC 35092 and ATCC51997.

To determine the protection provided by the vaccines groups of Dark Agouti rats (5-6 rats per group) aged 8-10 weeks old were immunized intra-tracheally (IT) with 50 uL of PBS or with 50 uL of PBS containing $5 \times 10^8$ killed NTHI-164 or NTHI-166, on days 0 and 14. On day 21 rats were infected with one of a panel of infection challenge NTHi strains. The rats were killed after 4 h of infection and lungs lavaged with 5×2 mL PBS to give 10 mL of bronchoalveolar lavage (BAL) fluid. The lungs were then homogenized in 10 mL PBS top give a lung homogenate (LH) suspension. Twenty microliter samples of serial 10-fold dilutions of BAL and LH were plated out on chocolate agar and incubated overnight at 37° C. in 5% $CO_2$ in air. The colonies were counted and the number of live NTHi in BAL and LH calculated for each rat. The levels of total bacteria in the lung were also determined for each rat by addition of bacteria number in BAL and LH. The mean bacteria level was calculated for each group of rats and the % bacterial clearance determined compared to the control PBS group as follows:

(Mean Bacteria in PBS Group−Mean Bacteria in Vaccine Group)×100 Mean Bacteria in PBS Group The percentage bacterial clearance in 4 hours is a measure of the degree of protection provided by the vaccine.

The mean percentage bacteria clearance provided by each test vaccine for the panel of 9 challenge infection strains was calculated. For the NTHI-164 vaccine the mean bacterial clearance for the panel was 84±4%, and for the NTHI-166 vaccine the mean bacteria clearance for the panel was 78±2%. This demonstrates that a vaccine prepared from killed NTHI-164 gives a greater degree of bacterial clearance against the panel of infecting strains than does a vaccine prepared from NTHI-166 and is thus more efficacious as a whole-cell vaccine.

Example 5: HI-164 Elicits a Non-Specific Immune Response Against Non-*Haemophilus* Species A multi-centre, double blind, placebo controlled, prospective study to assess safety and efficacy of orally administered killed whole cell non-typeable *Haemophilus influenzae* (NTHi) vaccine containing formalin-killed NTHI-164 (herein referred to as "HI-164OV") in preventing episodes of acute bronchitis in patients with moderate to severe airway disease.

1.18 Objectives & Methods 1.18.1 Primary Objectives (in Active Vs. Placebo Groups):

Compare number of acute bronchitis episodes

Compare proportion of patients with an episode of acute bronchitis

Compare duration of episodes of acute bronchitis 1.18.2 Methodology

Prospective, double blind, placebo controlled, parallel group, multi-centre study to assess the safety and efficacy of orally administered killed whole cell NTHi HI-164OV in preventing episodes of acute bronchitis in patients with moderate to severe ($FEV_1 \leq 50\%$ of the predicted value) airway disease.

Patients were randomly allocated in a 1:1 ratio to either study medication or placebo. Patients took medication on 3 consecutive days each month for 3 consecutive months. Microbiology evaluations were conducted on throat gargles for quantitative detection of Hi, and a sputum sample for Gram stain and quantitative detection of Hi and semi-quantitative detection of *M. catarrhalis, S. pneumoniae* and *Pseudomonas* species.

1.18.3 Number of Patients (Planned and Analyzed)

The study sample size was calculated on the basis of a 5% significance level and 80% power, a sample size of 50 participants per group would allow detection of:

A relative risk for infection of approximately 0.63 (i.e., relative risk reduction of 37%) assuming infection rate in the placebo group of 2;

An absolute reduction in the proportion of patients experiencing any infection of 28% (assuming 80% of placebo groups have any infection);

A relative risk for antibiotic prescribing of 0.67 (i.e., relative risk reduction of 33%) assuming a prescription rate of 2.4 in the placebo group;

A difference in mean days of duration of infections of 1.2 days (assuming standard deviation of duration of 2 days).

Assuming that 20% of participants did not complete the study, 62 needed to be recruited for each group with 124 to be randomized Actual number randomized and analyzed=38. There were two dropouts in each treatment group, with one in each group discontinuing the study due to an adverse event. Patients were recruited at 4 study centers. Note patient recruitment did not reach the planned number due to the limited available population with the required severity of illness who also met the inclusion criterion of 2 episodes of acute bronchitis per year in the previous 2 years at the 4 participating centers.

1.18.4 Product, Dose, & Batch Number

HI-164OV enteric-coated tablets: Contained 45 mg of formalin-inactivated NTHI-164 plus excipients. The lyophilized active substance is referred to as HI-164. Placebo enteric-coated tablets contained only excipients. Placebo and HI-164OV were stored at 2-8° C. and tablets weighed about 450 mg.

1.18.5 Administration & Study Duration

Patients took study medication orally with a glass of water, on an empty stomach, 30 minutes before breakfast on 3 consecutive days each month for 3 consecutive months (days 1-3, days 29-31 and days 57-59). Study duration was approximately 8 months.

Patients took study medication on 3 consecutive days each month for 3 consecutive months (days 1-3, days 29-31 and days 57-59). Study duration was approximately 8 months.

1.18.6 Criteria for Evaluation

The primary efficacy variables were:

Number of episodes of acute bronchitis

Proportion of patients on treatment experiencing an episode of acute bronchitis

The duration of acute bronchitis episodes

The number of courses of antibiotics for the treatment of acute episodes of bronchitis The presence of *H. influenzae, M. catarrhalis, S. pneumoniae* and *Pseudomonas* spp in sputum Severity of episodes of acute bronchitis

1.18.7 Statistical Methods

Statistical analyses were performed on the intention-to-treat population of 38 patients, namely all patients who were randomized to treatment regardless of whether they took study drug. All relevant data were summarized by treatment group. The analysis consisted of three sections:

Recruitment, and status at the end of the study

Baseline characteristics

Evaluation of treatment effects on the primary and secondary objectives.

The primary hypothesis tested was the superiority of HI-164OV over placebo in preventing episodes of acute bronchitis. The numbers of episodes of acute bronchitis were compared between groups using repeated measures GEE Poisson regression and the Cochran-Mantel Haenszel test. The proportion of participants in each treatment group who developed one or more episodes of acute bronchitis within the trial follow-up period were compared using Fisher's Exact Test. The duration of the acute bronchitic episodes was compared using the log-rank test and Wilcoxon rank-sum test.

Acute bronchitic episodes were adjudicated on the investigator reports and the adverse events which were of a respiratory infective nature; verification was obtained from the study site where needed. The number of courses of antibiotics for the treatment of the episodes of acute bronchitis was compared using the Cochran-Mantel Haenszel test. The total duration (number of days) of courses of antibiotics for the treatment of the acute episodes was compared using the Wilcoxon rank-sum test.

1.18.8 Patient Population Summary

The recruitment target of 124 randomized patients was not met; the actual number of patients screened was 42 of whom 38 were randomized and 34 completed the study. Of the patients randomized, there were 2 patients in each group who did not complete the study, of whom one patient in each group discontinued because of an adverse event. Baseline patient demographics were generally similar for the HI-164OV and placebo groups. The mean age of the population was about 70 years. More males than females were enrolled with 83.3% and 70.0% males and 16.7% and 30.0% females for the active and placebo groups, respectively. The mean $FEV_1$ in all patients was 0.95 liters/sec and similar between active and placebo groups; the median values were 1.00 and 0.85 in the active & placebo groups, respectively. A larger proportion of patients in both groups reported a history of smoking compared with never having smoked (84.2% smoking versus 15.8% never smoked). Patients had smoked for a mean of 51.36 pack years and a median of 45.5 pack years; with 45.0 & 46.0 median pack years for the active and placebo groups, respectively. At screening, 15.8% of all patients (with a similar distribution between the groups) still smoked.

Medical history was consistent with a population of patients of this age, the majority of whom smoked and had recognized airways disease. Significantly more patients reported a history of cardiac disorders in the placebo group compared with the HI-164OV group (13 (65%) vs. 5 (27.8%); p=0.028). There were no other statistically significant differences in the distribution of conditions between the groups according to system organ classes. With regards to respiratory disorders, COPD was reported 61.1% and 45.0% in the active and placebo groups, respectively; asthma reported in 33.3% and 10.0% in the active and placebo groups, respectively; bronchiectasis reported in 11.1% and 20.0% in the active and placebo groups, respectively; and emphysema reported in 22.2% and 35.0% in the active and placebo groups, respectively. Infections and infestations were reported in 8 (44.4%) of the HI-164OV group and 10 (50%) of the placebo group.

1.18.9 Primary Efficacy Variables

Number of Episodes of Acute Bronchitis:

Number of episodes of acute bronchitis: There were 22 episodes in 13 of 18 patients in the HI-164OV group and 29 episodes in 13 of 20 patients in the placebo group. The analysis of acute bronchitic episodes using monthly periods, showed a risk ratio of 0.83 [95% CI 0.47, 1.46], indicating a benefit for treatment but not achieving statistical significance (p=0.520). Analysis using three-monthly periods showed that the risk ratio was 0.84 [95% CI 0.48, 1.49], also indicating a benefit of treatment which was not statistically significant (p=0.397). However, whilst there was a similar rate of acute bronchitic events in the first 3 months of the study (0.82 events/100 patient days in each group), in the final months the rate was 0.85 in the placebo group but 0.60 in the HI-164OV group. This suggests a benefit of HI-164OV in this second period after all three cycles of drug had been administered although this was not significant (regression p values: period 0.894, treatment 0.397, interaction 0.533). The reduction of approximately 30% in the number of episodes in the second period is clinically relevant as the study began late in the autumn and a lag period of 6-8 weeks before benefit manifests is suspected from earlier studies.

When analyzed according to the period March-May versus the rest of the winter season, the treatment effect (risk ratio) was 0.92 [95% CI 0.50, 1.67], again suggesting an overall benefit of treatment with HI-164OV although this was not statistically significant (p=0.262). The rate of events in the groups during these periods was 0.69 events/100 patient days in the placebo group and 0.85 events/100 patient days in the HI-164OV group in March-May. In June-October the rate was 0.90 events/100 patient days in the placebo group and 0.59 events/100 patient days in the HI-164OV group.

Proportion of patients on treatment experiencing an episode of acute bronchitis: There was no statistically significant difference in the proportion of patients experiencing an episode of acute bronchitis in the two group (p=0.734).

The duration of acute bronchitis episodes: The median duration of acute bronchitic episodes in the HI-164OV group (8.5 days) was shorter compared with placebo (15.0 days), however, this was not statistically significant different (p=0.0879). However, there was a significant difference in the mean duration of episodes: 14.32±17.01 (SD) days in the HI-164OV group and 22.72±18.76 (SD) days in the placebo group (p=0.0141).

Analysis of the median time to the first episode of acute bronchitis was not statistically significantly different (81.0 days in the HI-164OV group and 100.0 days in the placebo group; p=0.7962).

The number of courses of antibiotics for the treatment of acute episodes of bronchitis: The number of patients treated with antibiotics for acute bronchitic episodes was similar between the HI-164OV and placebo groups (11 versus 13 respectively). In these same patients, there were fewer courses of antibiotics prescribed in the HI-164OV group (19 courses versus 48 for placebo); this difference was significant, p=0.031. (This calculation was based on a retrospective clinical review of the antibiotics prescribed for acute episodes of bronchitis). In addition, there were more patients with more courses of antibiotics in the placebo group (5 patients with 3 courses and 6 with ≥4 courses) than in the active group (1 patient with 3 courses and 1 with ≥4 courses). There was ≥75% reduction in the total number of days of antibiotic treatment for the acute bronchitic episodes; a total of 543 days in the placebo group and 136 in the HI-164OV group (p=0.013). The mean numbers of days of antibiotic therapy administered per patient was 41.77 days (range 5-117 days) in the placebo group and 12.36 days (range 1-41 days) in the HI-164OV group.

1.18.10 Secondary Efficacy Variables

Measure of surrogate mucosal immune markers of protection (NTHi-specific antibody in serum): Antibody to NTHi antigen was detected at the beginning and end of this example study. No significant difference was noted between placebo and active groups for either the mean levels or the degree of variation (determined by large SE bars) as had been noted in the HI-H003 study of subjects who smoked but most of whom were unaware of airways disease reflecting different levels of intrabronchial colonization. In those with moderate to severe COPD (HI-H002 study) there was a small but significant difference in the change in IgG anti NTHi antibody (0.15 of a $\log_{10}$; p=0.004) with a trend of a similar direction of a change for IgA anti NTHi antibody (0.09 of a $\log_{10}$; p=0.08). This significant treatment effect was not seen in those with an $FEV_1$ of >50% predicted. The mechanism is unclear. More frequent monitoring of the antibody response to treatment may provide a clearer picture of mechanism of change.

The presence of *H. influenzae, M Catarrhalis, S. Pneumoniae* & *Pseudomonas* spp in sputum: The bacteriology results of the sputum samples from this study showed consistent isolation of fewer non-NTHi pathogens (*Moraxella catarrhalis, Streptococcus pneumoniae*, and *Pseudomonas aeruginosa*) in those taking oral NTHi therapy. For example the total number of positive culture samples in the HI-1640V group were 34 and 66 in the placebo group of which *H influenzae* was isolated 17 and 22 times, respectively. The 'other pathogen' load was 17 isolates in the active group and 44 in the placebo group, these other colonizing pathogens being predominantly *Moraxella* species and *Pseudomonas* species. Four patients in the HI-1640V group and 8 in the placebo group had more than one bacterium isolated during the study. These results are consistent with the qualitative data in the earlier BRONCOSTAT™ studies. The general reduction in pathogen isolation noted following HI-1640V treatment is interpreted to reflect the non-specific nature of the final effector mechanism (i.e., phagocytosis) or the greater use of antibiotics in the placebo group.

Severity of episodes of acute bronchitis: There were no specific parameters specified in the protocol to measure the severity of acute bronchitic episodes. However, use of systemic corticosteroids and other concomitant medications for management of these episodes and also hospitalization of patients for respiratory events represent measures of severity. It was found that patients in the HI-164OV group received fewer treatments with systemic corticosteroids for episodes of acute bronchitis (4 in the HI-164OV group and 11 in the placebo group). There was also a marked difference in the number of days of systemic steroid treatment, although this was not statistically significant (HI-164OV group: 61 days (mean 15.25 days); placebo group: 289 days (mean 26.27 days); p=0.259). In addition, hospitalization to manage of adverse respiratory events were three times greater in the placebo group (n=7, 10 hospitalizations) than in the HI-164OV group (n=1, 1 hospitalization); this was statistically significant (p=0.0362).

1.19 Safety Results

Adverse events: The overall proportion of patients experiencing an AE in any primary system organ class was similar (18 (100%) in the HI-164OV group vs. 19 (95%) in the placebo group). The majority of reported AEs were mild or moderate, and were not considered to be related to study treatment; there was 1 patient in the HI-164OV group (patient 03 who had an episode of moderate gastroenteritis) and 2 in the placebo group (patient 14 who had moderate rash and a hot flush immediately after visit 1 and advised not to take more study medication; and patient 27 who had mild nausea) with events which were described as being possibly related to study treatment. No events were considered definitely related to study treatment.

One patient in the placebo group died as a result of an infective exacerbation of chronic airways limitation with *Pseudomonas* approximately 2 months after starting the study. The patient had completed two courses of study medication, and had been withdrawn from the study on 25 May 2006; he died on 6 Jul. 2006. The event was not considered to be related to study treatment. A total of eleven patients (3 patients (16.7%) in the HI-164OV group and 8 (40.0%) in the placebo group) reported serious adverse events (not statistically significant; p=0.160), but none were related to treatment. These eleven patients (3 in the HI-164OV group vs. 8 in the placebo group) were hospitalized a total of 15 times (3 events leading to hospitalization in the HI-164OV group versus 12 in the placebo group; p=0.0472). More than three times as many patients were hospitalized for management of a respiratory event in the placebo group (n=7, 10 hospitalizations) than in the HI-164OV group (n=1, 1 hospitalization); this was statistically significant (p=0.0362). The number of patients hospitalized for non-respiratory events was the same in both groups (2 patients).

This example study evaluated the effects of HI-164OV versus placebo as an add-on treatment in 18 and 20 patients, respectively, with moderate to severe airways disease (demonstrated by an $FEV_1$ of around 1.0 liters/sec and ≤50% of the predicted value) who had at least 2 episodes of acute bronchitis per year in the previous 2 years. Benefit of treatment with HI-164OV was observed in the primary endpoints, although, given the small size of the treatment groups, not all Analyses reached statistical significance. The higher number of patients with cardiac disease in the placebo group is likely to have negatively affected response to infection. Consistency of benefit was evident in the primary efficacy endpoints. There was a 16% risk reduction in the number of acute bronchitic episodes in the HI-164OV group and around a 35% reduction in the mean duration of these episodes (p=0.0141) compared with placebo. The effect of HI-164OV was evident in the first 3 months of therapy and maintained over the study. In addition, there was a 60% reduction in the courses of antibiotic employed to treat the bronchitic episodes and a 75% reduction of total days of antibiotic therapy. Eleven patients in the placebo group and 4 in the HI-164OV group received systemic (oral or intravenous) corticosteroids to manage the acute bronchitic episodes. These results were further supported by a reduction in hospitalization for respiratory events; there was a 80% reduction in the number of patients being hospitalized in those taking HI-164OV compared to placebo (7 vs. 1) and a 90% reduction in the number of hospitalizations (10 vs. 1). The rate of hospitalization for other reasons was the same between the 2 groups. Importantly, HI-164OV demonstrated an acceptable safety profile. There was no particular pattern of adverse events in the HI-164OV group and no overt issues detected in the vital signs or laboratory data.

The bacteriology data shows that there was a higher bacterial colonization of *H. influenzae* and also the other pathogens in the placebo group. This is interpreted as being related to the efficacy due to the efficacy of HI-164OV and also either due to or in spite of the higher use of antibiotics in the placebo group. There was a slight rise in the NTHi specific IgG and IgA levels.

The resulting data depicted in FIGS. 11 and 12 demonstrate the success of the specific antigen immune response and the non-specific immune system stimulation by HI-164OV. FIG. 11 shows the results of all patients (excluding sputum contamination) with respect to the number of infections experienced by a control group compared with the group of patients who had taken the recommended or suggested course of HI-164OV. These results demonstrated that there was a significant fall in infection rates not only with *H. influenzae* but also in respect of other organisms known to infect the airways (including, but not limited to: *M. catarrhalis, S. pneumoniae, Streptococcus* species, *P. aeruginosa, Pseudomonas* species, *S. aureus* and/or *Mycobacterium* species) and mucosal layers of patients. These results particularly highlight the fact that HI-164OV is generating both a specific and non-specific immune response in immunized patients.

Also importantly, the results of FIGS. 11 and 12 demonstrate that the specific and non-specific immune responses are approximately equal or balanced. In particular, the specific response against Hi limits or prevents the approximately same amounts of infections by secondary bacterial infections (such as by *M. catarrhalis, S. pneumoniae, P. aeruginosa, Pseudomonas* species and/or *Klebsiella pneumoniae*). Please note that for purposes of this specification "approximately equal" is defined as being within a range of 0-5 fold.

Please note that the results also demonstrate that for a non-specific immune response to occur, the patient is not required to be acutely infected or previously exposed with the primary bacterial antigen, which in this embodiment is NTHi. Therefore the oral vaccine described in this embodiment may effective in protecting or limiting the risk of infection in patients not previously exposed to NTHi or Hi for the oral vaccine to be successful.

The success of the results is further highlighted when the results are narrowed to investigate of a subgroup of the patients suffering from severe airways diseases such as COPD. The results of this subgroup are depicted in FIG. 12 and show even greater falls in infection rates with respect to these patients. Again, the HI-164OV has demonstrated effectiveness in use for generating both specific immune responses to Hi and non-specific immune responses to other bacterial organisms and thereby reducing the overall rates of infection. Please note that the non-specific immune responses may prevent or limit other bacterial infections of the mucosal layer or airways and fall within the scope of this specification.

In FIG. 13, the differences between BRONCOSTAT™ (as described in PCT Application No. WO86/05691) and HI-164OV are readily apparent. This table depicts the increase in stimulation index in the blood T-cells proliferation following the administration of the respective vaccines. Even after week 62, HI-164OV is stimulating T-cell proliferation whilst BRONCOSTAT™ fails to accomplish this in a statistically significant manner. The data in this table demonstrate the non-specific immune system stimulation by a vaccine of the present application.

Example 6: Physical Characteristics of Strain HI-164

1.20 Materials and Methods
1.20.1 Preparation of Whole Bacterial Extracts
Method I—Bacteria Grown on Chocolate Agar Plates A chocolate agar plate was inoculated with a single colony of NTHI-164 or other *Haemophilus influenzae* isolate. The plate was incubated overnight at 37° C.+5% $CO_2$. This resulted in heavy growth. The bacteria were removed from the surface of the plate with a sterile 10 µl loop and immersed into 0.5 mL of CelLytic B Cell Lysis Reagent in a microfuge tube. (Bacteria were dislodged by rubbing the loop between two fingers to twirl it while immersed in the lysis buffer). The tube was allowed to stand for 5 minutes to allow the bacteria to lyse completely. The tube was then centrifuged at 11,500 g for 5 minutes to pellet any insoluble cell debris. The supernatant was then carefully removed into a sterile microfuge tube and stored at −70° C. until required. The protein concentration of the sample was determined by performing a Protein Estimation Assay using the Pierce BCA protein assay kit.

Method II—Bacteria Grown in Tryptone Soya Broth+Htm Supplement

Tryptone Soya Broth base and HTM supplement were obtained from Oxoid.

To prepare the Tryptone Soya Broth with HTM supplement 12.5 gm of TSB powder was weighed out and place into 1 L Schott Bottle. Then 2.5 g of yeast extract was weighed out and added to the bottle. Distilled water (0.5 L) was added and the bottle shaken to dissolve the materials. The medium was then autoclaved for 15 minutes. The medium was allowed to cool overnight to room temperature. On day two, using sterile technique, 2 mLs of sterile distilled water was added to the vial of HTM Supplement using a 3 ml syringe and 19G needle. This was swirled to dissolve the solids and was stood at room temperature for 30 minutes. The contents of the vial were added to the bottle of medium using a sterile syringe and needle. The contents of the Schott bottle were mixed and labeled with the date. The medium was stored at 2-8° C. for up to 1 month. A chocolate agar plate was inoculated with a single colony of HI-164. and incubated overnight at 37° C.+5% $CO_2$. (This resulted in heavy growth). On day 3 100 mLs of the prepared TSB+HTM medium was measures into a 250 mL Erlenmeyer conical flask and pre-warmed in a 37° C. shaking incubator. A preparation of live NTHI-164 at $1\times10^{10}$ was prepared by harvesting the bacteria from the plate into PBS, measuring the optical density, comparing to a previously prepared plot of optical density versus bacteria concentration and adjusting the concentration as required. The broth was inoculated with 1.0×10¹⁰ live NTHI-164 (1 mL of 10¹⁰/mL) to give a starting concentration of 1×10⁸/mL and mixed by swirling. The bacterial suspension was incubated in the 37° C. shaking incubator for 11 hrs overnight. By this point the bacteria were at an optimal growth phase and expressing proteins of interest. To determine this an OD reading at 595 nm of the suspension was determined every half hour. When the OD had become stable, the growth curve had reached the stationary phase. 100 µl of the suspension was pipetted into a well of a flat bottom 96 well microtitre plate and read at a wavelength of 595 nm. The optical density was required to be between 0.5-1.0. If the suspension was higher than 1.0 it was adjusted by adding extra sterile broth to the flask. When adjusted 1.5 mL of the bacterial suspension was centrifuge at 11,500 g for 5 minutes. The supernatant was removed and the pellet re-suspended in 0.4 mL of CelLytic B. This was briefly vortexed and mixed for 5-10 minutes to ensure full extraction of the soluble proteins and was centrifuged again at 11,500 g for 5 minutes to pellet any insoluble cell debris. The supernatant was carefully removed into a sterile microfuge tube and stored at −70° C. until required. The protein concentration of the sample was determined by performing a Protein Estimation using the Pierce BCA protein assay kit.

1.20.2 Single Dimension Polyacrylamide Gel Electrophoresis

Twenty micrograms of protein from each extract was diluted to 20 uL with double-distilled water, and 10 uL of SDS-Stop solution was added. Samples were loaded into the wells of a 12% SDS-PAGE gel along with BIORAD precision molecular weight markers. Samples were run at 200V until the dye front reached the bottom of the gel. Gels were then stained with Sigma EZBlue stain.

1.20.3 Two-Dimensional Polyacrylamide Gel Electrophoresis

100 µg of each sample was acetone precipitated and resuspended in rehydration buffer. 7 cm, 3-10 NL IPG strips were used for the 1ˢᵗ dimension, with a total focusing time of 5 hours and 18750 Vhrs. IPG strips were loaded into the top of 12% i.5 mm thick SDS-PAGE gels and sealed with agarose. Molecular Weight Agarose plugs were also added to the top of the gels. Gels were run for 10 mins at 50V and then 45 mins at 200V. Gels were stained with Coomassie Blue and destained for 24 hrs. Gels were then scanned and spots detected.

1.20.4 MALDI Analysis of Proteins

Protein band or spots were excised from the SDS-PAGE gel and placed in 1.5 ml tubes. Bands were destained using 3 changes of 50% methanol/50 mM Ammonium Bicarbonate and air-dried overnight. Bands were then rehydrated using 200-400 ng of Trypsin dissolved in 20 mM Ammonium bicarbonate. After 10 minutes a further 5-10 µl of 20 mM ammonium bicarbonate were added to each band if necessary. Bands were incubated at 37° C. for 3 hours. Bands were then macerated and 1 µl samples removed. Samples were then mixed 1:1 with CHCA matrix and spotted onto a MALDI slide.

Samples were then analyzed using an Amersham ETTAN Maldi-ToF to generate a peptide mass fingerprint. Matches were searched for using the "nr" database as part of the analysis. Any samples that did not give good matches were then further searched using the "Swiss-Prot" database.

1.21 Results 1.21.1 Single Dimension Gels

Extracts of HI-164 and HI-166 were run on a single dimension gel. The gel picture is shown in the left panel of FIG. 14. The identity of bands is shown in the right panel of FIG. 14. Outer membrane protein 2 appears as two bands in the NTHI-164 gel and as one band in the NTHI-166 gel. This indicates differences in this protein in the two bacterial isolates and may account for the difference in protective capacity of the isolates. Two unidentified proteins present in NTHI-164 (MW 27 and 35) were not present in NTHI-166 and these proteins may also contribute to the superior protection provided by HI-164.

Figure 15:
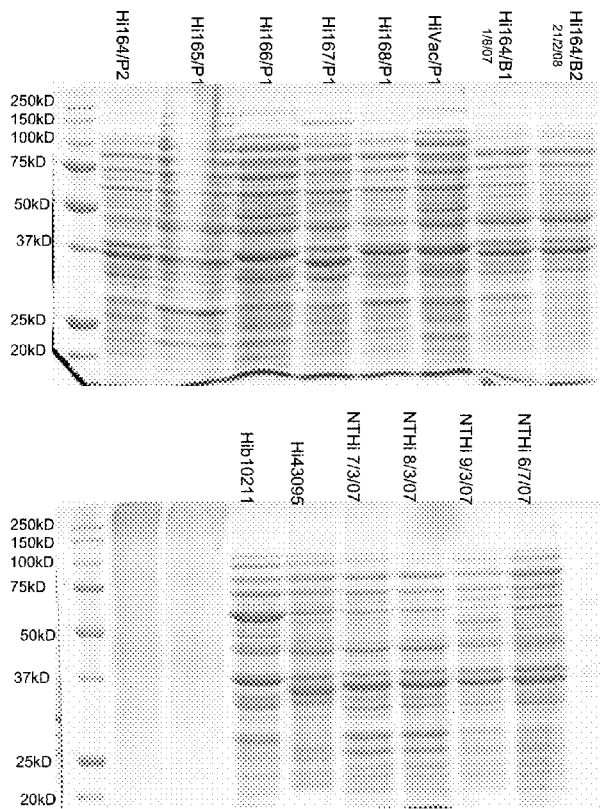
FIG. 15 shows the results of single dimension gels of extracts of various *Haemophilus influenzae* isolates/strains.

Single dimension gels were run for plate-grown HI-164 and other bacterial isolates, as shown in FIG. 15. Gels were also run from broth grown NTHI-164. The gel pattern for NTHI-164 is constant regardless of whether plate-grown or broth-grown and is different to that of other *Haemophilus influenzae* strains/isolates. The pattern most similar to that of the NTHI-164 is that of isolate NTHI-167.

1.21.2 Two Dimensional Gels

Figure 16A:
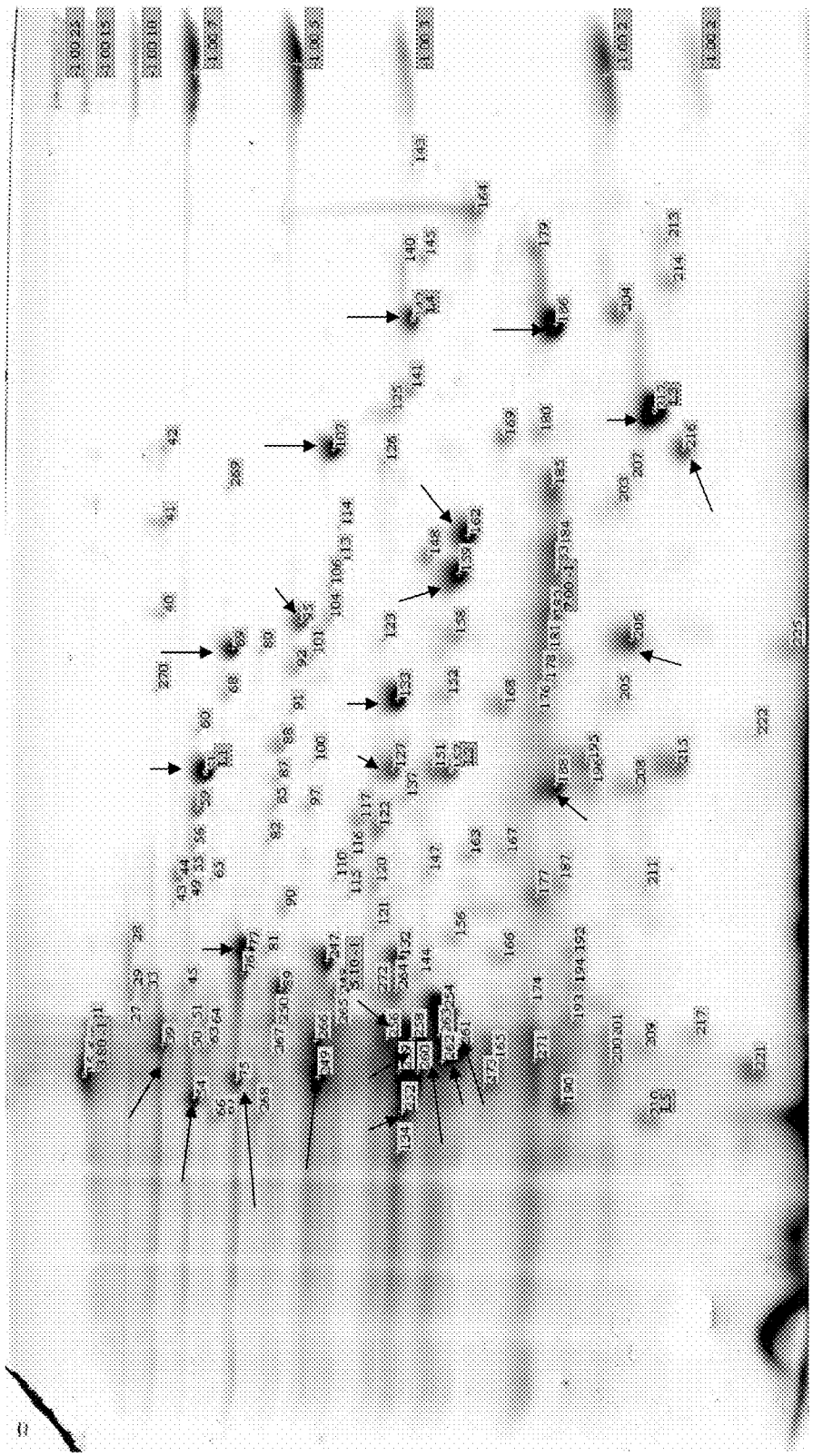
FIGS. 16A-16D shows the results of two-dimensional gel electrophoresis of various *Haemophilus influenzae* isolates/strains.
Figure 16B:
Figure 16C:
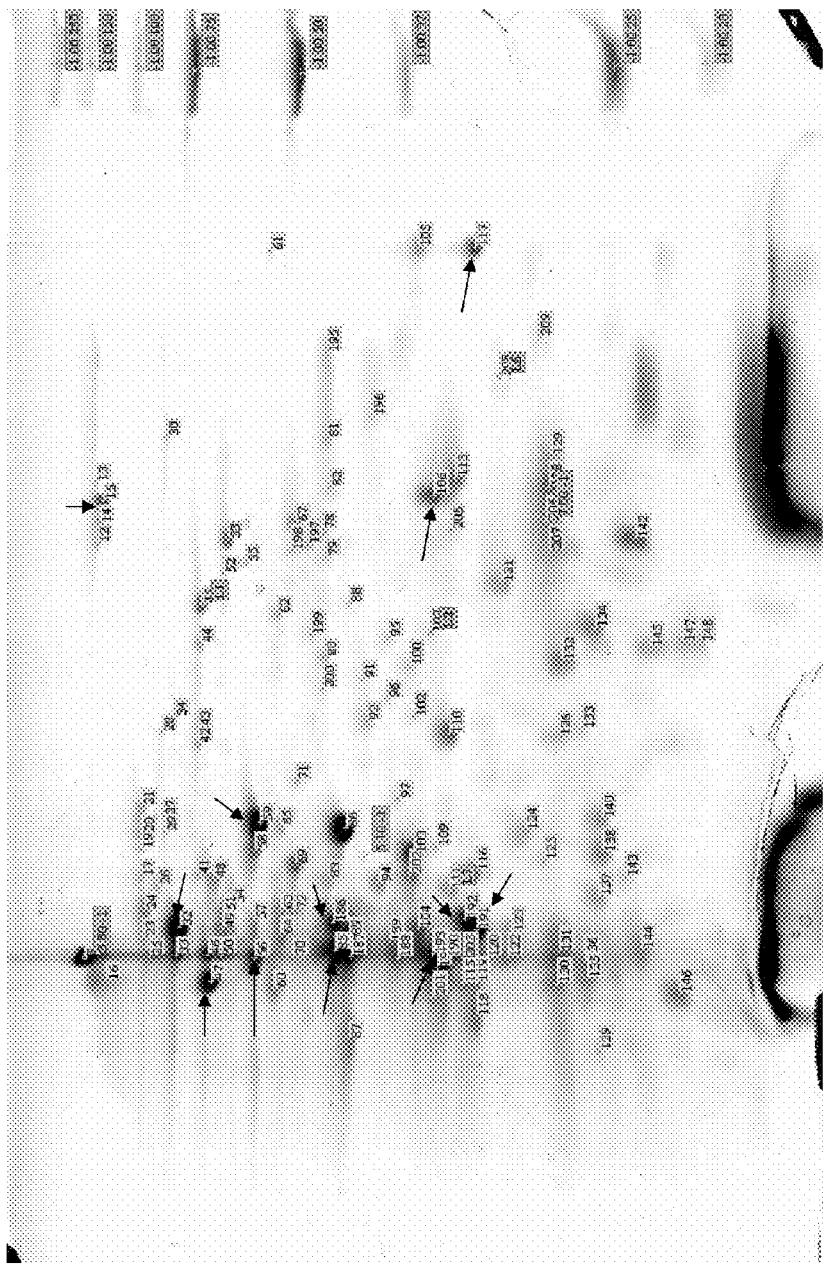
Figure 16D:
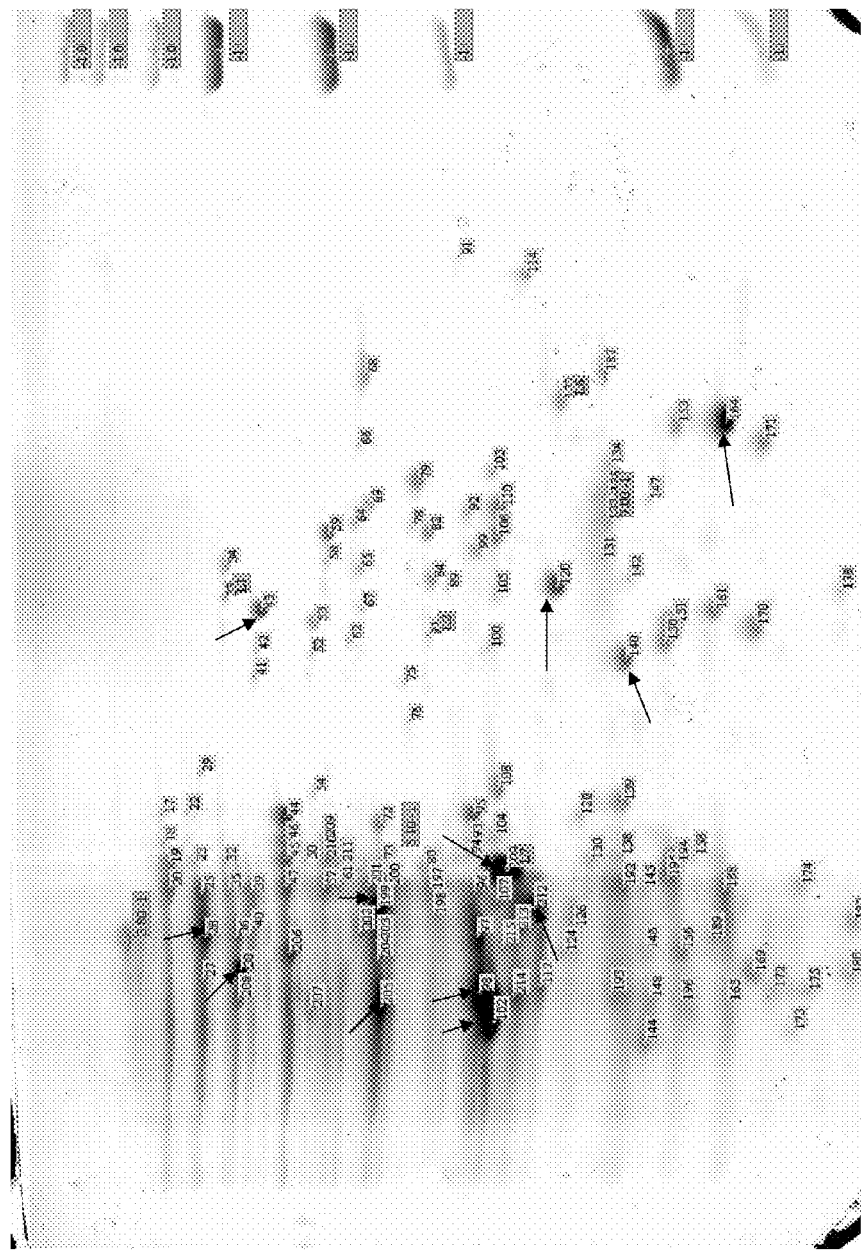

Two-dimensional gels were prepared from extracts of bacterial isolates grown on plates. The 2D gels are shown below in FIGS. 16A-16D. The 2D gel shows a difference in outer membrane protein P2 between HI-164 (FIG. 16A) and HI-166 (FIG. 13B) as there are two spots present in the HI-164 gel. The 2D gel of the HI-164 outer membrane protein preparation (i.e., outer membrane proteins extracted) (FIG. 16C) shows that the proteins in this preparation were predominantly OMP2 and OMP26.

1.21.3 MALDI Protein Analysis

Figure 14:
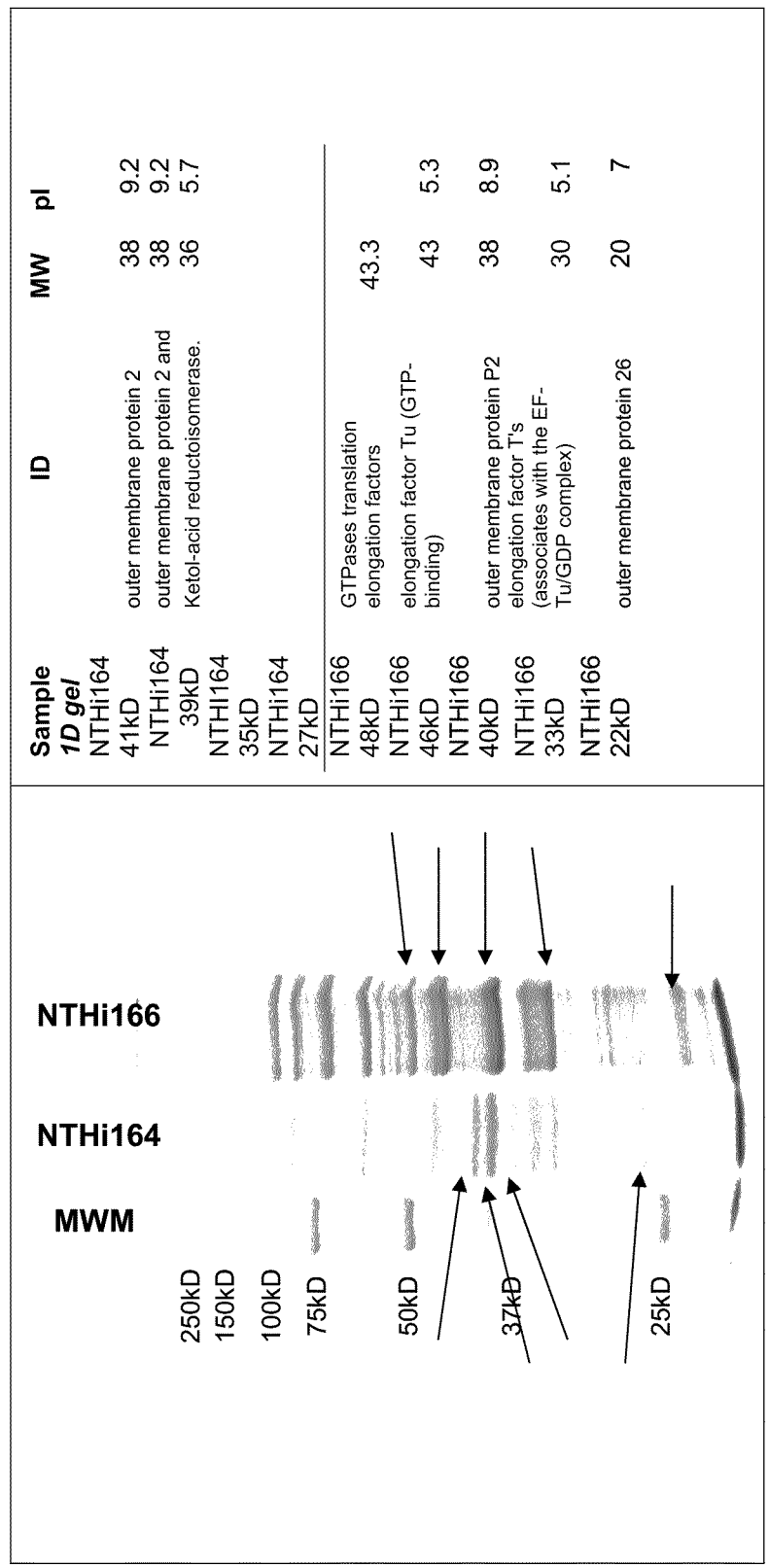
FIG. 14 shows the results of single dimension gel electrophoresis of extracts of HI-164 and HI-166.

The identity of bands sequenced from the single dimensional gels is shown in the right panel of FIG. 14. The identities of certain spots sequenced from the 2D gels are presented in Tables 11A through 11D below.

TABLE 11A

Identity of spots on 2D gel of HI-164 whole cell prep

| Sample | ID | MW | pI |
|---|---|---|---|
| spot 39 | translation elongation factors (GTPases) | 77 | 5 |
| spot 54 | molecular chaperone | 68.2 | 4.8 |
| spot 61 | 5'nucleotidase/2'3' cyclic phosphodiesterase and related esterases | 59.9 | 6.1 |
| spot 69 | ABC-type oligopeptide transport system, periplasmic component | 60.9 | 6.2 |
| spot 77 | Phosphoenolpyruvate carboxykinase [ATP]. | 59 | 5.4 |
| Spot75 | Phosphoenolpyruvate carboxykinase [ATP]. | 59 | 5.4 |
| spot 95 | Tryptophanase | 53 | 6.2 |
| spot 107 | Trypsin-like serine proteases, typically periplasmic, containing C-terminal PDZ domain | 49.1 | 7.7 |
| spot 127 | None | | |
| spot 133 | transglutaminase-like enzymes, putative cysteine proteases | 41.1 | 6.5 |
| spot 142 | Chain A, *Haemophilus influenzae* Ferric-binding protein Apo form | 33.7 | 7.9 |
| spot 159 | Chain A, O-acetylserine sulfhydrylase complex | 33.2 | 6.2 |
| spot 162 | | | |
| spot 184 | carbonic anhydrase | 28.7 | 6.6 |
| spot 186 | Phosphoribosyltransferase | 28.9 | 11 |
| spot 188 | | | |
| spot 254 | None | | |
| spot 206 | Superoxide dismutase [Mn]. | 24 | 6.2 |
| spot 212 | None | | |
| spot 216 | ribosome recycling factor | 20.75 | 6.8 |
| spot 249 | trigger factor | 48 | 5 |

TABLE 11A-continued

Identity of spots on 2D gel of HI-164 whole cell prep

| Sample | ID | MW | pI |
|---|---|---|---|
| spot 252 | Outer membrane protein P2. | 38 | 9.2[1] |
| spot 256 | D-galactose-binding periplasmic protein. | 33 | 5.3 |
| spot 259 | Outer membrane protein P2. | 38 | 9.1[1] |
| spot 261 | None | | |

[1]pI does not match with position on 2D gel

TABLE 11B

Identity of spots on 2D gel of HI-164 OMP prep

| Sample | ID | MW | pI |
|---|---|---|---|
| spot 126 | outer membrane protein P2 | 38 | 9.1 |
| spot 137 | ABC-type Zn2+ transport sytem, periplasmic component surface adhesin | 37.1 | 6.3 |
| spot 160 | FKBP-type peptidyl-prolyl cis-trans isomerases 1 | 26 | 6.8 |
| spot 168 | outer membrane protein 26 | 20 | 7 |
| spot 183 | | | |

TABLE 11C

Identity of spots on 2D gel of HI-166 whole cell prep

| Sample | ID | MW | pI |
|---|---|---|---|
| spot 28 | translation elongation factors (GTPases) | 77 | 5 |
| spot 38 | molecular chaperone | 68.2 | 4.8 |
| spot 43 | oligopeptide ABC transporter, periplasmic binding protein (oppA) | 60.45 | 6 |
| spot 98 | major outer membrane protein P2 | 39.99 | 9.2 |
| spot 102 | ABC-type Zn2+ transport sytem, periplasmic component surface adhesin | 37.8 | 6.4 |
| spot 107 | ABC-type sugar transport sytem, periplasmic component | 35.5 | 5.6 |
| spot 133 | TRAP-type C4-dicarboxylate transport system, periplasmic component | 36.4 | 6.9 |
| spot 140 | ABC-type amino acid transport/signal transduction systems, periplasmic component/domain | 26 | 8.8 |
| spot 164 | outer membrane protein 26 | 20.84 | 7.8 |
| spot 199 | Enolase | 46.2 | 5 |
| spot 205 | FKBP-type peptidyl-prolyl cis-trans isomerase (trigger factor) | 48.3 | 4.9 |
| spot 212 | translation elongation factorT's | 30.18 | 5.1 |

TABLE 11D

Identity of spots on 2D gel of HI-167 whole cell prep

| Sample | ID | MW | pI |
|---|---|---|---|
| spot 14 | None | | |
| spot 32 | translation elongation factors (GTPases) | 77 | 5 |
| spot 47 | None | | |
| spot 56 | molecular chaperone | 68.2 | 4.8 |
| spot 85 | FKBP-type peptidyl-prolyl cis-trans isomerase (trigger factor) | 48.3 | 4.9 |
| spot 86 | GTPases translation elongation factors | 43.36 | 5.2 |
| spot 106 | cysteine synthase | 33.4 | 6.5 |
| spot 117 | periplasmic ABC-type phosphate transport component | 36.65 | 9.2 |
| spot 156 | Enolase | 46.2 | 5 |
| spot 190 | None | | |
| spot 191 | None | | |
| spot 192 | Elongation Factor T's | 30 | 5.1 |

While various specific embodiments have been illustrated and described, it will be appreciated that various changes can be made without departing from the spirit and scope of the present application.

What is claimed is:

1. A pharmaceutical composition for the treatment of airways diseases, comprising an effective amount of killed non-typeable *Haemophilus* influenza isolates comprising isolate NTHi-164 deposited with the National Measurement Institute (NMI) and assigned deposit no. V08/021002 and isolate NTHi-167 deposited with the NMI and assigned deposit no. V08/021003, or the outer membrane protein fraction of isolated NTHi-167 or of isolate NTHi-164 and isolate NTHi-167, and wherein the composition is for oral administration.

2. The pharmaceutical composition of claim 1 comprising said membrane protein fraction of isolate NTHi-164.

3. The pharmaceutical composition of claim 1 which is in the form of a capsule, tablet, or enterically coated granules.

4. The pharmaceutical composition of claim 1 wherein the *Haemophilus influenzae* is formalin killed.

5. The pharmaceutical composition of claim 1 which further comprises a subenteric coating between said core and said enteric coating.

6. The pharmaceutical composition of claim 5 which further comprises a film coating as its outermost layer.

7. The pharmaceutical composition of claim 1 wherein said core comprises lactose.

8. The pharmaceutical composition of claim 1 wherein said core comprises cellulose or a cellulose derivative.

9. The pharmaceutical composition of claim 8 wherein said cellulose or cellulose derivative is croscarmellose sodium.

10. The pharmaceutical composition of claim 1 wherein said core comprises a filler.

11. The pharmaceutical composition of claim 10 wherein said filler is magnesium stearate.

12. The pharmaceutical composition of claim 1 wherein the weight of said core is 400 mg to 500 mg.

13. The pharmaceutical composition of claim 1 wherein the killed *Haemophilus influenzae* or the membrane protein fraction constitutes 7.5% to 15% of the weight of said core.

14. The pharmaceutical composition of claim 13 wherein the killed *Haemophilus influenzae* or the membrane protein fraction constitutes approximately 10% of the weight of said core.

15. The pharmaceutical composition of claim 5 wherein said subenteric coating comprises from a 2% to 3% of the weight of the core.

16. The pharmaceutical composition of claim 13 wherein said enteric coating comprises from a 10% to 12% of the weight of the core.

17. The pharmaceutical composition of claim 16 wherein said enteric coating is an aqueous acrylic coating.

18. The pharmaceutical composition of claim 6 wherein said film coating is purified water.

19. The pharmaceutical composition of claim 1 comprising from about $10^8$ to about $10^{13}$ killed colony forming units of said *Haemophilus influenzae* or said membrane protein fraction comprising from about $10^8$ to about $10^{13}$ killed colony forming units of said *Haemophilus influenza*.

20. A method of treating a patient with an airway disease, comprising administering to said patient an effective amount of a pharmaceutical composition according to claim 1.

21. The method of claim 20 wherein said effective amount is one to three unit doses of said pharmaceutical composition administered daily for two to five consecutive days, each unit does comprising from about $10^8$ to about $10^{13}$ killed colony forming units of said *Haemophilus influenzae* or a membrane protein fraction of from about $10^8$ to about $10^{13}$ killed colony forming units of said *Haemophilus influenzae*.

22. The method of claim 21 further comprising repeating said administration after a three to five week interval.

23. The method of claim 22 wherein said administration is repeated twice, each administration being repeated at a three- to five-week period following the preceding administration.

24. The method of claim 20 wherein said airway disease is chronic obstructive pulmonary disease or cystic fibrosis related disease.

25. The method of claim 24 wherein said chronic obstructive pulmonary disease is chronic bronchitis.

26. The method of claim 24 wherein said chronic obstructive pulmonary disease is emphysema.

27. The method of claim 24 wherein said chronic obstructive pulmonary disease is moderate to severe.

28. A method of treating asthma, comprising administering to a patient in need thereof an effective amount of a pharmaceutical composition according to claim 1.

29. The method of claim 28 wherein said effective amount is one to three unit doses of said pharmaceutical composition administered daily for two to five consecutive days, each unit dose comprising from about $10^8$ to about $10^{13}$ killed colony forming units of said *Haemophilus influenzae* or a membrane protein fraction of from about $10^8$ to about $10^{13}$ killed colony forming units of said *Haemophilus influenza*.

30. The method of claim 29 which further comprises repeating said administration after a three to five week interval.

31. The method of claim 30 wherein said administration is repeated twice, each administration being repeated at a three- to five-week period following the preceding administration.

32. The method of claim 28 wherein the asthma is intrinsic asthma.

33. Non-typeable *Haemophilus influenzae* isolate NTHi-167, deposited with the National Measurement Institute (NMI) and assigned deposit no. V08/021003, or the outer membrane protein fraction of NTHi-167.

34. Non-typeable *Haemophilus influenzae* isolate NTHi-167 of claim 33.

35. The pharmaceutical composition according to claim 1 wherein the composition comprises a dosage form having a core containing isolate NTHi-164 and isolate NTHi-167, or the outer membrane protein fraction of at least isolate NTHi-167 and an enteric coating surrounding the core.

* * * * *